US005498532A

United States Patent [19]

Katsumata et al.

[11] Patent Number: 5,498,532
[45] Date of Patent: Mar. 12, 1996

[54] PROCESS FOR PRODUCING AMINO ACIDS

[75] Inventors: Ryoichi Katsumata, Machida, Japan; Yasuhiro Kikuchi, Salt Lake City, Utah; Keiko Nakanishi, Machida, Japan

[73] Assignee: Kyowa Hakko Kogyo, Co., Ltd., Tokyo, Japan

[21] Appl. No.: 633,169

[22] Filed: Dec. 28, 1990

Related U.S. Application Data

[63] Continuation of Ser. No. 131,985, Dec. 11, 1987, abandoned.

[30] Foreign Application Priority Data

Dec. 13, 1986 [JP] Japan ................................. 61-296991
Jun. 26, 1987 [JP] Japan ................................. 61-159015

[51] Int. Cl.$^6$ ........................... C12P 13/04; C12M 15/77
[52] U.S. Cl. ...................... 435/106; 435/69.1; 435/107;
435/108; 435/110; 435/114; 435/115; 435/116;
435/172.3; 435/252.32; 435/320.1; 435/849
[58] Field of Search ................................. 435/69.1, 172.3,
435/253, 320.1, 106–116, 68.1, 252.32,
849

[56] References Cited

U.S. PATENT DOCUMENTS

| 4,411,991 | 10/1983 | Hirakawa et al. | 435/42 |
| 4,710,471 | 12/1987 | Katsumata | 435/72.3 X |
| 4,775,623 | 11/1988 | Katsumata | 435/114 |
| 4,927,758 | 5/1990 | Mizukami | 435/107 |

FOREIGN PATENT DOCUMENTS

| 82485 | 6/1983 | European Pat. Off. . |
| 190921 | 8/1986 | European Pat. Off. . |
| 215388 | 3/1987 | European Pat. Off. . |

OTHER PUBLICATIONS

Obata et al.; *Crem Abst* vol. 99 No. 28534 1983 "Isolation and Characterization of a Pentacrythitol–utilizing Bacterium".
Bezdek et al.; *Chem Abst* vol. 102 No. 188754 1987 "Interspecific Transfer of the *Serratia Col.* lactose operon using the transposen plasmid and its expression in *Agrobacterium tumefacians.*"vol. 103 No. 79167r 1985 "Recombinant DNA having a phosphoenolpyrosate carboylase gene inserted therein bacteria carrying said recombinant DNA and a process of producing amino acids using said bacteria".
Sanchez et al., *Chem Abst* vol. 170 232b 1986 "Construction of plasmids capable of automatic replication in *Corynebacterium* and/or *Brevibacterium Bacillus subtilis* and *scherichia coli*".
JP Patent 6/260892, Accession No. 87–002443/01 Patent Date No. 19, 1986. Abstract only.
JP Patent 60210994, Accession No. 86–02392 Patent Date Oc. 23, 1985 Abstract only.
Yanase et al., *J. Ferment. Technol.* 66:409–415 1988.
Okayama et al., *Mol. Cell biology* vol. 2 No. 2 pp. 161–170 Feb. 1982 "High–efficiency cloning of full–length BNA".
Han et al., *Biochemistry* vol. 26 No. 6, 1987 pp. 1617–1623 1987 "Isolation of full–length DNA using improved methods for m RNA vsole Hun and CDNA cloning."Coleclesgy et al. *Gene* vol. 31, p. 35 1985.
Carey et al., *Chem Abst* vol. 104 No. 466745S "Expression of the lactose operon in *Zymomanas Mobilis*" 1986.
Morinagu et al., *Chem Abst* vol. 105 No. 204186m 1986 "Shuttle vectors for promotor detection in coryneform bacteria".
S. Horinouchi, Proteins/Nucleic Acids/Enzymes, 28, 1468 (1983).
Goldfarb, D. S. et al., Nature, 293, 309 (1981).
Taxonomical Studies on Glutamic Acid Producing Bacteria Part I, pp. 328–334, 1965.
New versatile plasmid vectors for expression of hybrid, etc. . . . , Casadaban, et al Gene, 25, 71, (1983).
Kagaku to Seibutsu, vol. 20, No. 1, pp. 47–58.

*Primary Examiner*—John L. LeGuyader
*Attorney, Agent, or Firm*—Antonelli, Terry, Stout & Kraus

[57] ABSTRACT

The invention relates to coryneform microorganisms capable of assimilating lactose which carry a recombinant DNA capable of conferring the ability to assimilate lactose on coryneform microorganisms; and to a process for producing L-amino acids which comprises culturing said coryneform microorganism capable of assimilating lactose in a culture medium containing lactose to form an amino acid, and recovering said amino acid accumulated in the culture broth. Further, the invention relates to a method for preparing recombinant plasmids containing a DNA fragment essential to the expression of a gene in coryneform microorganisms.

5 Claims, 2 Drawing Sheets

PROCESS FOR PRODUCING AMINO ACIDS

This application is a continuation of application Ser. No. 131,985, filed Dec. 11, 1987, now abandoned.

BACKGROUND OF THE INVENTION

As the processes for producing amino acids by using glutamic acid-producing coryneform bacteria belonging to the genus *Corynebacterium* or *Brevibacterium*, there have been known processes for producing glutamic acid by using wild-type strains of such genus and processes for producing various amino acids by using mutant strains derived from wild-type strains of such genus ["Amino Acid Fermentation, (I) and (II)" Association of Amino Acid and Nucleic Acid (Kyoritsu Shuppan, 1972); and "Amino Acid Fermentation" by Aida, Takinami and Chibata (Gakkai Publishing Center, 1986)]. Further, plasmid vectors for glutamic acid-producing coryneform bacteria [Japanese Published Unexamined Patent Application No. 134500/82 (European Patent No. 58889, U.S. Pat. No. 4617267), Japanese Published Unexamined Patent Application No. 183799/82 (European Publication No. 63763, U.S. Pat. No. 4500640) and Japanese Published Unexamined Patent Application No. 105999/83 (European Publication No. 82485, U.S. patent application Ser. No. 668674)], and methods for the transformation of these bacteria [Japanese Published Unexamined Patent Application No. 186492/82 (European Publication No. 63764, U.S. Pat. No. 4683205) and Japanese Published Unexamined Patent Application No. 186489/82 (European Publication No. 64680, U.S. Pat. No. 4681847)] have been recently developed. As a result, recombinant DNA technology has now become applicable to strains of the genus *Corynebacterium* or *Brevibacterium*, whereby new aspects on the effective utilization of these microorganisms have been opened.

The recombinant DNA technology has made it possible to clone a gene responsible for an enzyme that catalyzes the rate-limiting reaction in the biosynthetic pathway of an amino acid-producing microorganism and to introduce a recombinant DNA containing the cloned gene into a host microorganism, thereby enhancing the activity of said rate-limiting enzyme. There have been already known the cases in which amino acid productivity of coryneform bacteria has been increased by introduction of a recombinant DNA containing a cloned gene derived from a coryneform bacterium or from a microorganism of different species such as *Escherichia coli* [Japanese Published Unexamined Patent Application No. 126789/83 (European Publication No. 88166, U.S. patent application Ser. No. 787010), Japanese Published Unexamined Patent Application Nos. 156292/84, 156294/84, 24192/85, 34197/85, 30693/85 and 66989/85 (U.S. patent application Ser. Nos. 073888, 580814, 613209, 631648, 631649 and 646512) (European Publication No. 136359)]. Fermentation of these microorganisms of the genus *Corynebacterium* or *Brevibacterium* for the production of various amino acids is carried out by using, as the main carbon source, glucose, fructose, sucrose, maltose, acetic acid, ethanol, lactic acid or substances containing the same (for example, starch hydrolyzate and cane molasses), which these strains are hereditarily able to assimilate.

Attempts have also been made to use lactose as a carbon source for the production of amino acids by microorganisms belonging to the genus *Corynebacterium* or *Brevibacterium*. However, lactose cannot be employed as the main carbon source because the glutamic acid-producing coryneform bacteria have no ability to assimilate lactose [Nogeikagaku Kaishi, 39,328 (1965)]. The mixed culture is a known example of the process for producing amino acids by fermentation in which lactose is used as a carbon source. In the process, a lactose-assimilating bacterium (e.g., a lactobacillus) and an amino acid-producing bacterium belonging to the genus *Corynbacterium* or *Brevibacterium* are simultaneously cultured in a medium containing lactose, whereby lactose is assimilated into lactic acid by the former, and the latter assimilates lactic acid to produce glutamic acid, lysine or valine (Japanese Published Unexamined Patent Application Nos. 174095/82, 170194/82 and 208993/82).

Whey which is generated in large quantities as liquid waste from the cheese and casein manufacturing processes generally contains about 5% lactose and about 1% proteins. Although a part of it is used as food, animal feed additives and fertilizers, it is discarded for the most part. This is undesirable not only from the viewpoint of utilization of resources but also from that of environmental protection from pollution [The Food Industry, 18 No. 12, 20 (1975)]. Hence, use of whey as a fermentation material, if possible, would be of great industrial significance, as it would contribute to the effective utilization of resources and the environmental protection. The aforementioned mixed culture for the production of glutamic acid and other amino acids is intended for the utilization of lactose contained in whey, but it suffers various disadvantages. If lactic acid fermentation by the lactose-assimilating bacterium progresses rapidly, the culture broth becomes acidic, whereby the amino acid fermentation by the coryneform bacterium is inhibited. Accordingly, the amounts of the two strains to be inoculated and culture conditions must be elaborately determined according to the lactic acid-assimilating activity of the amino acid-producing strain belonging to the genus *Corynebacterium* or *Brevibacterium* which is used in the mixed culture. Thus, intricate operations and strict culture control are required. Under the circumstances, the present inventors tried to confer, by recombinant DNA technology, the ability to assimilate lactose on strains of *Corynbacterium* or *Brevibacterium* which genetically lack this ability in order to develop a new fermentation process for producing various amino acids in which a microorganism of *Corynbacterium* or *Brevibacterium* alone is cultured in a medium containing a lactose-containing substance such as whey as a carbon source.

This improvement of amino acid-producing bacteria by introduction of a recombinant DNA is based on the amplification effect of enzyme genes which are capable of expression in a coryneform bacterium. The expression of these genes takes place under the control of expression regulatory region inherent to the donor microorganism of these genes. Therefore, in some cases, the expression of the genes in a host microorganism may not be so efficient and the amino acid productivity can not be markedly improved. The expression efficiency of introduced genes must be enhanced in a suitable way to ensure a high amino acid productivity.

It is generally accepted that a promoter region necessary for the initiation of transcription and a ribosome-binding sequence essential to messenger RNA translation must be positioned upstream of a structural gene in order to ensure the expression of the gene in a microorganism, and that expression efficiency of the gene depends mainly on the activity of the promoter. Since the promoter region and the ribosome-binding sequence are considered to have species-specific base sequences, efficient expression of a desired structural gene would be achieved by disposing the structural gene downstream of a highly active promoter region and a proper ribosome-binding sequence derived from the host microorganism. Such an efficient gene expression system has already been established for *Escherichia coli* whose mechanism of gene expression has been reported in detail [Nakamura, K., Kagaku To Seibutsu, 20, 47 (1982)] and for *Bacillus subtilis* on which detailed genetic analysis has also been made [Horinouchi, S., Proteins/Nucleic Acids/Enzymes, 28, 1468 (1983); Goldfarb, D. S. et al., *Nature*, 293, 309 (1981)].

As a method for preparing a promoter region derived from a coryneform bacterium, there has been reported the use of a promoter-probing vector carrying a promoter-less chloramphenicol resistance gene which is used for detection of promoter activity (Japanese Published Unexamined Patent Application No. 124387/86). This vector contains the chloramphenicol resistance gene of *Escherichia coli* except its promoter region, that is, the structural gene and ribosome-binding sequence of that gene, and further has a promoter cloning site upstream therefrom. A DNA fragment containing the premoter region of a coryneform bacterium can be obtained by inserting a DNA fragment derived from the coryneform bacterium into this cloning site and selecting a recombinant plasmid which can confer chloramphenicol resistance on coryneform bacteria. It is considered that transcription of the chloramphenicol resistance gene in the recombinant plasmid thus obtained starts at the promoter region derived from the coryneform bacterium to form a messenger RNA, and translation of the messenger RNA is started by the function of the ribosome-binding sequence originated from the sequence of *Escherichia coli* chloramphenicol resistance gene, leading to the expression of the gene. However, the species-specificity in the gene-expression control region mentioned above suggests that insertion of a highly active promoter derived from a coryneform bacterium does not necessarily ensure efficient gene expression, because the ribosome-binding sequence of *Escherichia coli* might be unsuitable for translation in coryneform bacteria and hence translation might be rate-limiting in the expression process. Thus, it would be desirable to clone a DNA fragment having both a transcription initiation site and a translation initiation site in order to obtain a gene-expression control region which ensures efficient gene expression in coryneform bacteria. However, no effective method has so far been known to isolate such a DNA fragment.

It has been found that microorganisms belonging to the genus *Corynebacterium* or *Brevibacterium* can be imparted with the ability to assimilate lactose by introducing the genetic information derived from *Escherichia coli* lactose operon into a strain of the genus *Corynbacterium* or *Brevibacterium* by recombinant DNA technology and expressing the introduced information.

Further, intensive studies have been made to isolate the promoter region and the ribosome-binding sequence responsible for the initiation of transcription and translation, respectively, which are both essential to the expression of a gene in coryneform bacteria, from a chromosomal DNA. As a result, a plasmid vector has been constructed which has autonomous replicability in a coryneform bacterium, and contains a DNA fragment carrying structural genes coding for β-D-galactosidase, or coding for β-D-galactosidase and β-galactoside permease derived from *Escherichia coli* lactose operon, and can be used to clone a DNA fragment responsible for the gene expression control in coryneform bacteria. The present invention has been accomplished based on these findings.

SUMMARY OF THE INVENTION

The present invention relates to coryneform microorganisms capable of assimilating lactose which carry a recombinant DNA containing genetic information derived from *Escherichia coli* lactose operon and capable of conferring the ability to assimilate lactose on microorganisms belonging to the genus *Corynbacterium* or *Brevibacterium* by the expression of the information; and to a fermentation process for producing L-amino acids which comprises culturing said coryneform microorganism capable of assimilating lactose in a culture medium containing lactose to form an amino acid, and recovering said amino acid accumulated in the culture broth. Hence, the present invention is related to the bioindustry, particularly to the manufacture of amino acids useful in the pharmaceutical, food and animal feed industries.

The present invention further relates to a method for preparing recombinant plasmids containing a DNA fragment essential to the expression of a gene in coryneform bacteria belonging to the genus *Corynebacterium* or *Brevibacterium*. Such recombinant plasmids are useful for obtaining DNA fragments which have functions necessary to enable or enhance the expression of desired genes in coryneform bacteria, and thereby for enabling the improvement of metabolite productivity of coryneform bacteria, the conferment of new functions on coryneform bacteria and the production of useful enzymes and physiologically active proteins in coryneform bacteria.

Figure 1:
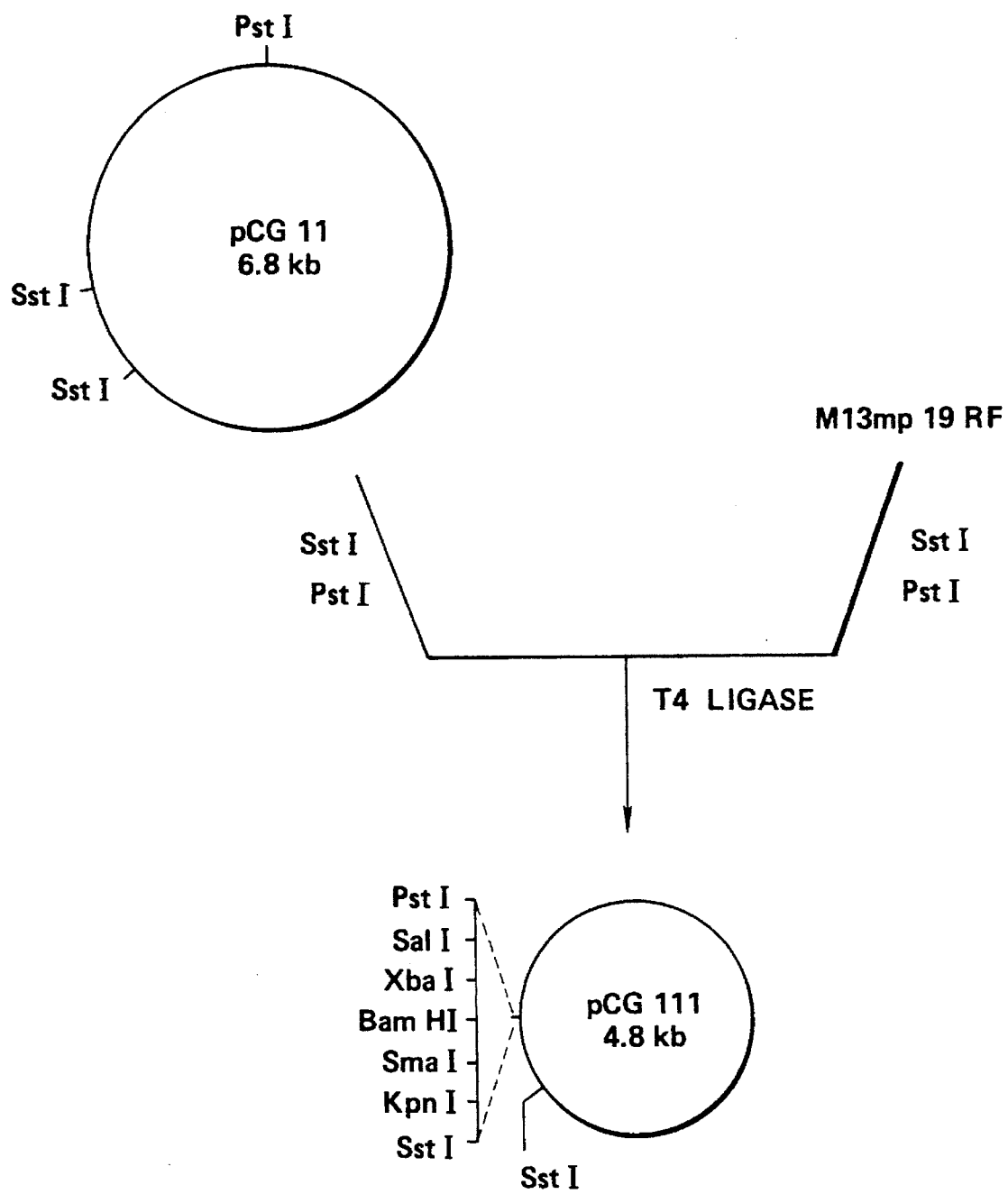
FIG. 1 illustrates the steps for constructing pCG111.

In both of these figures, the sizes of plasmid DNAs are expressed in kilobase (kb).

DETAILED DESCRIPTION OF THE INVENTION

The present invention relates to a coryneform microorganism capable of assimilating lactose and carrying a recombinant DNA which confers the ability to assimilate lactose on a microorganism belonging to the genus *Corynbacterium* or *Brevibacterium*, said recombinant DNA comprising (a) a part or all of the coding region of the structural genes for β-D-galactosidase and β-galactoside permease derived from *Escherichia coli* lactose operon, and (b) a DNA fragment derived from a microorganism belonging to the genus *Corynbacterium* or *Brevibacterium* and enabling expression of foreign genes in strains belonging to the genus *Corynbacterium* or *Brevibacterium*, which is positioned upstream of the coding region of said structural genes; and to a process for producing amino acids which comprises culturing said coryneform bacterium capable of assimilating lactose in a culture medium containing lactose to produce an amino acid, and recovering said amino acid accumulated in the culture broth.

The utility of the invention is to allow the production of various L-amino acids by fermentation using, as a carbon source, lactose contained in whey which is produced in large quantities as a waste in the cheese and casein manufacturing processes and now discarded for the most part. This process for conferring the ability to assimilate lactose on coryneform bacteria belonging to the genus *Corynbacterium* or *Brevibacterium*, which are inherently unable to assimilate lactose, by recombinant DNA technology, and thereby enabling the production of various amino acids by direct fermentation using, as a carbon source, lactose or lactose-containing substance such as whey has been first established by the present invention.

Amino acids that can be produced by the process established by the present invention include glutamic acid, glutamine, lysine, threonine, isoleucine, valine, leucine, tryptophan, phenylalanine, tyrosine, histidine, arginine, ornithine, citrulline and proline.

The present invention also relates to a method for preparing a recombinant plasmid containing a DNA fragment responsible for the initiation of transcription and translation necessary for the expression of a gene in a microorganism belonging to the genus *Corynbacterium* or *Brevibacterium*, which comprises (a) inserting a DNA fragment derived from a microorganism belonging to the genus *Corynbacterium* or *Brevibacterium* into a plasmid at a restriction enzyme cleavage site, said plasmid having autonomous replicability in a microorganism of the genus *Corynebacterium* or *Brevibacterium* and containing selectable genetic markers, a DNA fragment derived from *Escherichia coli* lactose operon and carrying the coding region of structural genes necessary for the expression of β-D-galactosidase activity, and restriction enzyme cleavage sites positioned just before said coding region; (b) transforming a strain of the genus *Corynbacterium* or *Brevibacterium* by using the recombinant plasmid thus prepared to obtain a transformant having the ability to assimilate lactose; and (c) isolating the recombinant plasmid from said transformant.

The plasmid used for cloning the DNA fragment responsible for the initiation of transcription and translation in a coryneform bacterium may be prepared by any method, so long as it has autonomous replicability in a strain of the genus *Corynebacterium* or *Brevibacterium*, and contains selectable genetic markers, the structural genes coding for β-D-galactosidase, or coding for β-D-galactosidase and β-galactoside permease derived from *Escherichia coli* lactose operon, and restriction enzyme cleavage sites positioned just before said structural genes. For example, it may be prepared by isolating a DNA fragment containing lacZ (structural gene for β-D-galactosidase) and lacy (structural gene for β-galactoside permease) from lactose operon of *Escherichia coli* K12 strain, and ligating it to a plasmid vector autonomously replicable in a strain of the genus *Corynbacterium* or *Brevibacterium* and having a suitable selection marker.

Any strain belonging to the genus *Corynbacterium* or *Brevibacterium* and having an ability to produce an amino acid may be used as the host microorganism in the present invention. Preferred examples are the strains listed below and mutants derived therefrom.

| | |
|---|---|
| *Corynebacterium glutamicum* | ATCC 13032 |
| *Corynebacterium acetoacidophilum* | ATCC 13870 |
| *Corynebacterium herculis* | ATCC 13868 |
| *Corynebacterium lilium* | ATCC 15990 |
| *Brevibacterium divaricatum* | ATCC 14020 |
| *Brevibacterium flavum* | ATCC 14067 |
| *Brevibacterium immariophilium* | ATCC 14068 |
| *Brevibacterium lactofermentum* | ATCC 13869 |
| *Brevibacterium thiogenitalis* | ATCC 19240 |

Wild-type strains may be used for producing glutamic acid and glutamine, but it is preferred to use mutants with improved productivity (for example, the mutants described in Japanese Published Unexamined Patent Application Nos. 66990/85 and 148094/80). Various amino acid-producing strains constructed by known mutagenesis or recombinant DNA technology may be used for producing other amino acids.

The genetic information on lactose assimilation can be obtained from the lactose operon relating to this function in *Escherichia coli* K12 strain. The lactose operon has been investigated in most detail among the genes of *Escherichia coli*, and its structure and expression mechanism have been elucidated almost completely ["The Lactose Operon" by J. R. Beckwith; Cold Spring Harbor Laboratory (1982)]. The lactose operon contains three structural genes, i.e. lacZ, lacy and lacA which are located in that order and are transcribed as a single transcription unit. The genes lacZ, lacy and lacA code for β-D-galactosidase, β-galactoside permease and galactoside acetyltransferase, respectively, and β-D-galactosidase and β-galactoside permease are essential to assimilation of lactose. Lactose is taken in through a cell membrane by the action of B-galactoside permease, and hydrolyzed into galactose and glucose by the action of β-D-galactosidase, and the galactose and glucose thus formed are then metabolized through the general metabolic pathway.

Conferment of the ability to assimilate lactose on a strain of the genus *Corynbacterium* or *Brevibacterium* depends on whether or not the genes coding for β-D-galactosidase and β-galactoside permease derived from *Escherichia coli* lactose operon can be expressed in that strain. Actually, however, when a recombinant plasmid which contains lactose operon including the transcription and translation signals derived from *Escherichia coli* is used, its genetic information is expressed in a strain of the genus *Corynbacterium* or *Brevibacterium* but feebly, failing to confer the ability to assimilate lactose on the strain. This fact indicates that the expression of a gene must be sufficiently intense in order to confer the ability to assimilate lactose on a strain of the genus *Corynbacterium* or *Brevibacterium*. Therefore, it is necessary to construct such a new recombinant plasmid that the genes coding for β-D-galactosidase and β-galactoside permease derived from *Escherichia coli* lactose operon contained therein are able to be fully expressed in a strain of the genus *Corynbacterium* or *Brevibacterium*.

The present inventors have found that *Escherichia coli* lactose operon is expressed in a strain of the genus *Corynbacterium* or *Brevibacterium* sufficiently to confer the ability to assimilate lactose on the strain by replacing the transcription and translation signals in *Escherichia coli* lactose operon by the transcription and translation signals derived from a strain of the genus *Corynbacterium* or *Brevibacterium*.

A recombinant plasmid which contains *Escherichia coli* lactose operon and allows such efficient gene expression as to confer the ability to assimilate lactose on a microorganism of the genus *Corynbacterium* or *Brevibacterium* can be prepared by inserting a DNA fragment, which is derived from a strain of the genus *Corynbacterium* or *Brevibacterium* and enables sufficient expression of *Escherichia coli* lactose operon in said strain, into a plasmid at a site upstream of the structural genes derived from *Escherichia coli* lactose operon. For example, such a plasmid can be constructed according to the following procedure: isolating a DNA fragment containing the structural genes, lacZ and lacY, from the lactose operon of *Escherichia coli* K12 strain; ligating this DNA fragment to a plasmid vector autonomously replicahie in strains of the genus *Corynbacterium* or *Brevibacterium*; further inserting a DNA fragment derived from a strain of the genus *Corynbacterium* or *Brevibacterium* and enabling expression of foreign genes at a site upstream of the coding region of lacZ and lacY; and selecting a recombinant plasmid which can confer the ability to assimilate lactose on a strain of the genus *Corynebacterium* or *Brevibacterium*.

The DNA fragment containing a part or all of the coding region of the structural genes lacZ and lacY in lactose operon can be isolated by self-cloning of lactose operon according to the known in vitro recombination technique ("Molecular Cloning" by T. Maniatis, et al.; Cold Spring Harbor Laboratory, 1982) using the *Escherichia coli* host-vector system with a mutant derived from *Escherichia coli* K12 strain unable to assimilate lactose as a recipient, and with restoration of the ability to assimilate lactose, followed by subcloning of the structural genes, lacZ and lacY, by the use of suitable endonucleases and exonucleases. Alternatively, a DNA fragment which contains the structural genes lacZ and lacY already subcloned may be used; for example, plasmid pMC1871 which contains the structural gene lacZ and was prepared by Casadaban, et al. [Gene, 25, 71 (1983)] is preferably used. The plasmid pMC1871 is a vector for the detection of the promoter activity of *Escherichia coli*. This plasmid contains a DNA fragment derived from *Escherichia coli* lactose operon, which lacks the promoter region and the region coding for eight N-terminal amino acids of β-D-galactosidase and contains the region encoding from the codon for the ninth amino acid to the EcoRI cleavage site located on the 5'-side of the codon for C-terminal amino acid. In addition, the coding region is preceded by multiple cloning site. In vitro recombination of pMC1871 at a site downstream of its lacZ-coding region with a DNA fragment containing lacY-coding region from *Escherichia coli* lactose operon separately cloned gives a DNA fragment which does not contain the transcription and translation signals of *Escherichia coli* and contains structural gene lacy and a part of structural gene lacZ lacking a region coding for some N-terminal amino acids of β-D-galactosidase.

The DNA fragment containing the coding region of both lacZ and lacY thus obtained is then ligated to a vector of a strain of the genus *Corynbacterium* or *Brevibacterium*.

Any vector autonomously replicable in a strain of the genus *Corynebacterium* or *Brevibacterium* may be used. Examples of such vectors include pCG1 [Japanese Published Unexamined Patent Application No. 134500/82 (European Patent No. 58889, U.S. Pat. No. 4617267)], pCG2 [Japanese Published Unexamined Patent Application No. 35197/83 (European Patent No. 73062, U.S. Pat. No. 4489160)], pCG4 and pCG11 [Japanese Published Unexamined Patent Application No. 183799/82 (European Publication No. 63763, U.S. Pat. No. 4500640)], pCE54 and pCB101 [Japanese Published Unexamined Patent Application No. 105999/83 (European Publication No. 82485, U.S. patent application Ser. No. 668674)], pCE51, pCE52 and pCE53 [Mol. Gen. Genet., 196,175 (1984)], and plasmids derived therefrom. These vector plasmid DNAs can be isolated from cultured cells of the strains containing the same and purified according to the methods disclosed in Japanese Published Unexamined Patent Application No. 134500/82 (European Patent No. 58889, U.S. Pat. No. 4617267) and Japanese Published Unexamined Patent Application No. 186489/82 (European Publication No. 64680, U.S. Pat. No. 4681847).

The DNA fragment containing the structural genes lacZ and lacY cloned in the Escherichia coli host-vector system can be isolated by digestion with a restriction enzyme, followed by agarose gel electrophoresis. Separately, the vector plasmid is cleaved with a restriction enzyme which gives cleaved terminals capable of being ligated with the above DNA fragment. The two elements are then ligated by treatment with T4 ligase, and the ligase reaction mixture is used to transform a strain of the genus *Corynbacterium* or *Brevibacterium* by the method using protoplasts [Japanese Published Unexamined Patent Application No. 186489/82 (European Publication No. 64680, U.S. Pat. No. 4681847), Japanese Published Unexamined Patent Application No. 186492/82 (European Publication No. 63764, U.S. Pat. No. 4683205) and Japanese Published Unexamined Patent Application No. 126789/83 (European Publication No. 88166, U.S. patent application Ser. No. 787010)]. Transformants are selected based on the selective marker of the vector. Plasmid can be obtained from the transformants, followed by analysis of their structure by digestion with restriction enzymes. The desired plasmid must have restriction enzyme cleavage sites upstream of the coding region of lacZ and lacY in order to allow, in the subsequent step, the construction of a plasmid enabling the expression of the genes coding for β-D-galactosidase and β-galactoside permease. Plasmid pE'lacl disclosed in the Example of the present invention is prepared by ligating the lacZ-lacY DNA fragment obtained above to pCG1111 at its oligolinker site which is derived from M13mp19RF DNA, and hence has a desired structure wherein several restriction enzyme cleavage sites derived from oligolinker are positioned just before the lacZ-lacY structural genes.

A DNA fragment responsible for the initiation of transcription and translation in a strain of the genus *Corynbacterium* or *Brevibacterium* can be cloned by using said plasmid containing the structural genes lacZ and lacY and by detection of the expression of the gene as a detection marker. Any of the microorganisms known as coryneform bacteria belonging to the genus *Corynebacterium* or *Brevibacterium* may be used as the donor of the aforementioned DNA fragment and as the host microorganism for cloning. Preferred examples are the strains listed below and mutants derived therefrom.

| | |
|---|---|
| *Corynebacterium glutamicum* | ATCC 13032 |
| *Corynebacterium glutamicum* | ATCC 31833 |
| *Corynebacterium acetoacidophilum* | ATCC 13870 |
| *Corynebacterium herculis* | ATCC 13868 |
| *Corynebacterium lilium* | ATCC 15990 |
| *Brevibacterium divaricatum* | ATCC 14020 |
| *Brevibacterium flavum* | ATCC 14067 |
| *Brevibacterium immariophilium* | ATCC 14068 |
| *Brevibacterium lactofermentum* | ATCC 13869 |
| *Brevibacterium thiogenitalis* | ATCC 19240 |

Cloning of the DNA fragment responsible for the initiation of transcription and translation in a strain of the genus *Corynbacterium* or *Brevibacterium* by the use of the above plasmid can be carried out in the following manner.

The plasmid is cleaved at the restriction enzyme cleavage site located just before the region coding for the structural genes lacZ and lacY. Separately, the chromosomal DNA of a strain of the genus *Corynebacterium* or *Brevibacterium*, which is the donor of a DNA fragment enabling the expression of a gene, is completely or partially digested with the same restriction enzyme as used above or another restriction enzyme which gives the same cohesive ends. The two digestion mixtures thus obtained are ligated by treatment with T4 ligase, and the ligase reaction mixture is used to transform the protoplast of a strain of the genus *Corynbacterium* or *Brevibacterium*. The protoplast suspension thus obtained is spread on a regeneration agar medium containing a vector marker reagent and 5-bromo-4-chloro-3-indolyl-β-D-galactopyranoside (X-GAL).

Corynform bacteria originally show no β-D-galactosidase activity, but the colonies of transformants which express this activity encoded by the structural gene lacZ show blue color on the selection medium. The recombinant plasmid having the DNA fragment responsible for the initiation of transcription and translation in coryneform bacteria, which is inserted upstream of the structural gene lacZ, can be isolated from cultured cells of the blue-colored transformants by a conventional method.

The development of blue color in colonies is caused by the hydrolysis of X-GAL with β-D-galactosidase, and therefore, a colony having a high β-D-galactosidase activity shows a deep blue color. Strains carrying the recombinant DNA which contains a DNA fragment responsible for the initiation of transcription and translation in coryneform bacteria to enable intense gene expression can be easily detected as deep blue colonies. The degree of gene expression in a blue-colored transformant can be correctly evaluated by subjecting cultured cells of the blue-colored transformant to ultrasonic disruption and measuring the β-D-galactosidase activity in the cell-free extract.

A shuttle vector for *Escherichia coli* and coryneform bacteria can be prepared by combining the plasmid obtained above which contains a DNA fragment carrying promoter region and ribosome-binding sequence derived from a coryneform bacterium with a vector autonomously replicable in *Escherichia coli*. The degree of gene expression of said promoter in *Escherichia coli* can be examined by introducing the shuttle vector into *Escherichia coli*. The degree of expression of β-D-galactosidase in *Escherichia coli* under the control of the promoter region and ribosome-binding sequence derived from a coryneform bacterium was determined by the method described below in Example (6). The result, as shown in Table 2, has revealed that a promoter-ribosome-binding sequence which allows an intense gene expression in a coryneform bacterium does not always show a high degree of expression in *Escherichia coli*. This fact indicates the difference between the region responsible for the initiation of transcription and translation in coryneform bacteria and that in *Escherichia coli*. It was thus confirmed that not only the promoter but also the region responsible for the initiation of translation must be derived from a coryneform bacterium in order to ensure full gene expression in coryneform bacteria.

The process established by the present invention to prepare the region responsible for the initiation of transcription and translation provides an effective means for obtaining the gene-expression control region for coryneform bacteria.

The DNA fragment carrying gene-expression controlling region and cloned on a plasmid as described above can be isolated by cleaving the plasmid with suitable restriction enzymes according to the cleavage map of that plasmid, followed by fractionation with agarose gel electrophoresis. The DNA fragment thus isolated is then inserted, by known recombinant DNA technology, into a plasmid at a site upstream of a desired structural gene to construct a recombinant DNA. By introducing the recombinant DNA into a coryneform bacterium, efficient synthesis of the desired gene product in the bacterium can be achieved. If the expression of a structural gene coding for an enzyme responsible for the biosynthesis of a metabolite such as an amino acid is intensified by this process, the productivity of the metabolite will be significantly increased. It is also possible to confer a new metabolic function which is not inherent in coryneform bacteria such as the ability to assimilate lactose, or to give an ability to produce physiologically active proteins derived from eukaryotes by expression of a structural gene derived from foreign microorganisms or eukaryotes.

Plasmid pE'lacI, which enables cloning of the DNA fragment responsible for the transcription and translation in coryneform bacteria, was introduced into *Corynbacterium glutamicum* ATCC 31833, and the transformant thus obtained was deposited with the Fermentation Research Institute (FRI), Agency of Industrial Science and Technology, Japan on Sep. 27, 1986 as *Corynbacterium glutamicum* K73 (FERM BP-1178).

A recombinant DNA which can confer the ability to assimilate lactose on a strain of the genus *Corynbacterium* or *Brevibacterium* is derived from the plasmid autonomously replicable in a strain of the genus *Corynbacterium* or *Brevibacterium* and containing a DNA fragment which carries the structural genes lacZ and lacY in the following manner. That is, the said plasmid is cleaved with a restriction enzyme at the cleavage site located just before the structural genes. Separately, in order to obtain a DNA fragment enabling expression of foreign genes, the chromosomal DNA of a strain of the genus *Corynbacterium* or *Brevibacterium* is completely or partially digested with the same restriction enzyme as used above or another restriction enzyme which gives the same cleaved terminals. The two digestion mixtures thus obtained are ligated by treatment with T4 ligase, and the ligase reaction mixture is used to transform the protoplast of a strain of the genus *Corynbacterium* or *Brevibacterium*. The protoplast suspension thus obtained is spread on regeneration agar medium containing a vector marker reagent and X-GAL which enables detection of a clone having β-D-galactosidase activity. Transformants which have acquired the ability to assimilate lactose can be isolated by selecting blue-colored colonies grown on the selection agar medium, and a strain which can grow using lactose as a single carbon source can be selected from these transformants. A strain of the genus *Corynbacterium* or *Brevibacterium* becomes capable of assimilating lactose by transformation with the plasmid isolated from the transformant obtained above.

This fact indicates that the ability to assimilate lactose is conferred by said plasmid. Thus, a recombinant plasmid which can confer the ability to assimilate lactose on a strain of the genus *Corynbacterium* or *Brevibacterium* can be constructed. One example of such a recombinant plasmid is pCPL7 derived from pE'lacI, in which a DNA fragment of 3.1 kb obtained by cleavage of the chromosomal DNA of a strain of the genus *Corynbacterium* with restriction enzyme Sau3A has been inserted at a site upstream of the structural gene lacZ of pE'lacI to enable expression of foreign genes.

The recombinant plasmid which can confer the ability to assimilate lactose thus prepared can be introduced into various amino acid-producing strains of the genus *Corynbacterium* or *Brevibacterium* by the above-described method using protoplasts.

Examples of the microorganisms into which this recombinant plasmid is to be introduced include the strains known as glutamic acid-producing coryneform bacteria such as *Corynbacterium glutamicum*, *Corynbacterium herculis*, *Brevibacterium flavum* and *Brevibacterium lactofermentum*. Transformants actually obtained are shown in the Example described later. A typical example is *Corynbacterium glutamicum* K74, which is a transformant obtained by introducing plasmid pCPL7 into *Corynbacterium glutamicum* ATCC 31833. This strain was deposited with FRI on Sep. 27, 1986 as *Corynbacterium glutamicum* K74 (FERMBP-1179).

The coryneform bacterium capable of assimilating lactose thus prepared takes in lactose through the cell membrane by the action of β-galactoside permease, hydrolyzes it into galactose and glucose by the action of β-D-galactosidase, and produces an amino acid by utilizing the glucose formed.

Production of amino acids by the strains carrying such a recombinant plasmid may be carried out by the same culture method as in the case where glucose or molasses is used as a carbon source. That is, the transformant is cultured under aerobic conditions in a medium containing, as a carbon source, a lactose-containing substance in place of glucose or molasses, and other nutrients such as nitrogen sources, inorganic compounds, amino acids and vitamins at a controlled temperature and pH, whereby a desired L-amino acid can be produced in the culture broth. In general, loss of plasmid is likely to occur during the culturing of plasmid-carrying strains. In the process of the present invention, strains which have lost the recombinant plasmid fail to grow in the medium containing a lactose-containing substance as the main carbon source, and consequently, the recombinant plasmid is stably retained.

Lactose-containing substances such as cheese whey, casein whey, and products obtained therefrom by extraction or concentration can be used as a carbon source, as well as lactose itself.

Further, as the carbon source, carbohydrates such as glucose, glycerol, fructose, sucrose, maltose, mannose, starch, starch hydrolyzate, molasses, etc.; polyalcohols; and various organic acids such as pyruvic acid, fumaric acid, lactic acid, acetic acid, etc. can be used. Furthermore, hydrocarbons, alcohols, etc. can be used, depending upon the assimilability of the microorganism to be used.

As the nitrogen source, ammonia; inorganic or organic ammonium salts such as ammonium chloride, ammonium sulfate, ammonium carbonate and ammonium acetate; urea and other nitrogen-containing inorganic substances; and nitrogen-containing organic substances such as peptone, NZ-amine, meat extract, yeast extract, corn steep liquor, casein hydrolyzate, fish meal or its digested product and chrysalis hydrolyzate may be used.

As the inorganic compound, dipotassium hydrogen phosphate, potassium dihydrogen phosphate, ammonium sulfate, ammonium chloride, magnesium sulfate, sodium chloride, ferrous sulfate, manganese sulfate, calcium carbonate, etc. may be used. If vitamins, amino acids, etc. required for the growth of the microorganism are supplied by other medium components described above, it is not necessary to add these specific nutrients separately to the medium.

Culturing is carried out under aerobic conditions by shaking culture, aeration-stirring culture, etc. The preferred culturing temperature is generally 20°–40° C. It is desirable that the pH of the culture medium is maintained around neutrality. L-amino acids is usually accumulated in the culture medium after culturing for 1–5 days under these conditions. After completion of the culturing, the cells are removed from the culture broth, and L-amino acid is recovered from the supernatant by a known method established for the particular amino acid.

For the production of L-glutamic acid using, as a carbon source, molasses which contains biotin at a high concentration, various methods have been proposed: a method in which an antibiotic such as penicillin is added (Japanese Published Examined Patent Application No. 1695/62), a method in which a surface-active agent or a saturated fatty acid is added (Japanese Published Examined Patent Application Nos. 8798/65 and 14559/65), a method in which an oleic acid-requiring strain is used (Japanese Published Examined Patent Application No. 19632/75) and a method in which a glycerol-requiring strain is used (Japanese Published Examined Patent Application No. 33997/76). Since whey also generally contains biotin at a high concentration, the above methods may be employed advantageously in the production of L-glutamic acid using whey as a carbon source.

Thus, lactose-containing substances can be used as the main carbon source for the production of various amino acids such as L-glutamic acid, L-glutamine, L-lysine, L-threonine, L-isoleucine, L-valine, L-leucine, L-tryptophan, L-phenylalanine, L-tyrosine, L-histidine, L-arginine, L-ornithine, L-citrulline and L-proline by amino acid-producing strains of the genus $Corynbacterium$ or $Brevibacterium$ carrying a recombinant plasmid which can confer the ability to assimilate lactose.

Certain specific embodiments of the present invention are illustrated by the following representative example.

EXAMPLE (1) Cloning of $Escherichia\ coli$ lactose operon

Chromosomal DNA was isolated from cultured cells of $Escherichia\ coli$ K294 (FERM BP-526), which was derived from $Escherichia\ coli$ K12 and having the ability to assimilate lactose, according to the method of Marmurk. et al. [J. Mol. Biol., 3,208 (1961) ].

pBR322 [Gene, 2, 95 (1975)] commercially available from Takara Shuzo Co., Ltd. was used as a cloning vector.

Four units of restriction enzyme BglII (a product of Takara Shuzo Co., Ltd.) was added to 90 µl of reaction buffer solution for BglII [10 mM tris (hydroxymethyl) aminomethane (hereinafter referred to as Tris), 10 mM $MgCl_2$, 100 mM NaCl and 1 mM dithiothreitol, pH 7.5] containing 2 µg of the chromosomal DNA prepared above. The mixture was subjected to reaction at 37° C. for 60 minutes. Then, the reaction was stopped by heating the reaction mixture at 65° C. for 10 minutes. Separately, 2 units of restriction enzyme BamHI (a product of Takara Shuzo Co., Ltd. ) was added to 90 µl of reaction buffer solution for BamHI (10 mM Tris, 10 mM $MgCl_2$, 100 mM NaCl and 1 mM dithiothreitol, pH 7.5) containing 1 µg of pBR322 DNA. The mixture was subjected to reaction at 37° C. for 60 minutes. Then, the reaction was stopped by heating the reaction mixture at 65° C. for 10 minutes.

Both reaction mixtures were mixed, and then 20 µl of buffer solution for T4 ligase at a 10-fold concentration (660 mM Tris, 66 mM $MgCl_2$ and 100 mM dithiothreitol, pH 7.6), 2 µl of 100 mM ATP and 350 units of T4 ligase (a product of Takara Shuzo Co., Ltd.) were added thereto. The mixture was subjected to ligase reaction at 12° C. for 16 hours. The reaction mixture was used for the transformation of $Escherichia\ coli$ K72 (lac$^-$, leu$^-$), which was derived from $Escherichia\ coli$ K12 and deposited with FRI as $Escherichia\ coli$ K72 FERM BP-1176 on Sep. 27, 1986.

The transformation was carried out according to the method of Dagert, et al. [Gene, 6, 23 (1979)]. $Escherichia\ coli$ K72 strain was inoculated into 50 ml of L-medium (10 g/l Bacto-tryptone, 5 g/l yeast extract, 1 g/l glucose and 5 g/l NaCl, pH 7.2), and cultured at 37° C. until the optical density (OD) measured at 660 nm with a Tokyo Koden colorimeter reached 0.5 (hereinafter OD is measured at 660 nm unless otherwise specified). The culture broth was cooled on ice for 10 minutes and centrifuged. The cells collected were suspended in 20 ml of cooled 0.1M $CaCl_2$ and the suspension was left standing at 0° C. for 20 minutes. After centrifugation of the suspension, the collected cells were resuspended in 0.5 ml of 0.1M $CaCl_2$ and the suspension was left standing at 0° C. for 18 hours. To this suspension of $CaCl_2$-treated cells (150 µl), was added 50 µl of the ligase reaction mixture obtained above. The resulting mixture was left standing at 0° C. for 10 minutes and then heated at 37° C. for 5 minutes. L-medium (2 ml) was further added thereto and shaking culture was carried out at 37° C. for 2 hours.

The culture broth thus obtained was spread on L-agar-medium (L-medium containing 16 g/l agar) containing 100 µg/ml ampicillin and 40 µg/ml X-GAL, and incubation was carried out at 37° C. for one day. The blue-colored colonies grown on the agar medium were collected, and their properties were examined. It was found that this strain could grow on a minimal medium containing lactose as a carbon source and leucine (10 g/l lactose, 7 g/l $K_2HPO_4$, 2 g/l $KH_2PO_4$, 0.5 g/l disodium citrate dihydrate, 1 g/l $(NH_4)_2SO_4$, 0.1 g/l $MgSO_4 \cdot 7H_2O$, 0.1 mg/l thiamine hydrochloride, 50 mg/l leucine and 16 g/l agar, pH 7.2) but could not grow on L-agar-medium containing 25 µg/ml tetracycline.

From this transformant, a plasmid DNA was isolated according to the method of Ann, et al. [J. Bacteriol., 140, 400 (1979)]. The plasmid DNA was digested with restriction enzymes, and analyzed by agarose gel electrophoresis. It was found that the plasmid had a size of 15.3 kilobase (kb), and a structure wherein a BglII-cleaved DNA fragment of 11 kb derived from the chromosomal DNA of *Escherichia coli* K294 strain was inserted in pBR322 at the BamHi-cleavage site. This plasmid was named pLacI.

(2) Construction of novel vector plasmid pCG111

A novel vector pCG111 was constructed by ligating vector pCG11 [Japanese Published Unexamined Patent Application No. 183799/82 (European Publication No. 63763, U.S. Pat. No. 4500640)] autonomously replicahie in *Corynbacterium glutamicum* with a multilinker contained in M13mp19RF DNA according to the procedure described below.

pCG11 was isolated from cultured cells of *Corynbacterium glutamicum* ATCC 39019 (a lysozyme-sensitive mutant derived from *Corynbacterium glutamicum* ATCC 31833) carrying pCG11 in the following manner.

The above mutant was cultured with shaking at 30° C. in 400 ml of NB medium (20 g/l bouillon powder and 5 g/l yeast extract, pH 7.2) until OD reached about 0.7. The cultured cells were collected, washed with TES buffer solution [0.03M Tris, 0.005M disodium ethylenediaminetetraacetate (EDTA) and 0.05M NaCl, pH 8.0], and suspended in 10 ml of a lysozyme solution (25% sucrose, 0.1M NaCl, 0.05M Tris and 0.8 mg/ml lysozyme, pH 8.0). The suspension was subjected to reaction at 37° C. for 2 hours. Then, 2.4 ml of 5M NaCl, 0.6 ml of 0.5M EDTA (pH 8.5) and 4.4 ml of a solution comprising 4% sodium laurylsulfate and 0.7M NaCl were successively added to the reaction mixture, and the mixture was gently stirred and placed on ice for 15 hours. The mixture was then transferred to a centrifuge tube and centrifuged at 69,000×g at 4° C. for 60 minutes to recover a supernatant. Then, polyethylene glycol (PEG) 6000 (a product of Nakarai Chemicals, Ltd.) was added thereto in an amount corresponding to 10% by weight. The mixture was gently stirred, and then placed on ice. After 10 hours, the mixture was centrifuged at 1,500×g for 10 minutes to recover pellets.

Then, 5 ml of TES buffer solution was added to gradually dissolve the pellets, and 2.0 ml of 1.5 mg/ml ethidium bromide was added to the solution. Cesium chloride was further added to adjust the density of the solution to 1.580.

The solution thus obtained was subjected to ultracentrifugation at 105,000×g at 18° C. for 48 hours, and a high density band at the lower position of the centrifuge tube detected under ultraviolet irradiation was withdrawn by puncturing the side of the centrifuge tube, using a 21-gauge needle to recover pCG11 plasmid DNA. The fraction was treated five times with an equal volume of isopropyl alcohol solution [90% (V/V) isopropyl alcohol in TES buffer solution] containing a saturated amount of cesium chloride to remove ethidium bromide by extraction. Then, the solution was dialyzed against TES buffer solution.

To 90 µl of reaction buffer solution for restriction enzyme SstI (10 mM Tris, 10 mM $MgCl_2$ and 1 mM dithiothreitol, pH 7.5) containing 1 µg of pCG11 plasmid DNA obtained above, was added 1 unit of SstI (a product of Takara Shuzo Co., Ltd.), and the mixture was subjected to reaction at 37° C. for 60 minutes. Then, 10 µl of 1M NaCl and 1 unit of PstI (a product of Takara Shuzo Co., Ltd.) were added thereto, and the reaction was continued at 37° C. for an additional 60 minutes and then stopped by heating the reaction mixture at 65° C. for 10 minutes.

Similarly, 1 µg of M13mp19RF DNA (a product of Takara Shuzo Co., Ltd.) was digested with SstI and PstI, and the reaction was stopped by heating. Both reaction mixtures were mixed, and then 20 µl of buffer solution for T4 ligase at a 10-fold concentration, 2 µl of 100 mM ATP and 350 units of T4 ligase were added thereto. The mixture was subjected to ligase reaction at 12° C. for 16 hours. The reaction mixture was used for the transformation of *Corynebacterium glutamicum* ATCC 31833.

The transformation was carried out by using the protoplasts prepared in the following manner. A seed culture of *Corynbacterium glutamicum* ATCC 31833 cultured in NB medium was inoculated into semi-synthetic medium SSM [20 g/l glucose, 10 g/l $(NH_4)_2SO_4$, 3 g/l urea, 1 g/l least extract, 1 g/l $KH_2PO_4$, 0.4 g/l $MgC_2 \cdot 6H_2O$, 10 mg/l $FeSO_4 \cdot 7H_2O$, 0.2 mg/l $MnSO_4 \cdot 4-6H_2O$, 0.9 mg/l $ZnSO_4 \cdot 7H_2O$, 0.4 mg/l $CuSO_4 \cdot 5H_2O$, 0.09 mg/l $Na_2B_4O_7 \cdot 10H_2O$, 0.04 mg/l $(NH_4)_6Mo_7O_{24} \cdot 4H_2O$, 30 µg/l biotin and 1 mg/l thiamine hydrochloride, pH 7.2 (hereinafter referred to as SSM medium)], and cultured with shaking at 30° C. When OD reached 0.2, penicillin G was added to the culture medium to a concentration of 0.5 unit/ml, and culturing was continued until OD reached 0.6.

The cells were collected from the culture broth, and suspended to a concentration of about 109 cells per milliliter in RCGP medium [5 g/l glucose, 5 g/l Casamino acid, 2.5 g/l yeast extract, 3.5 g/l $K_2HPO_4$, 1.5 g/l $KH_2PO_4$, 0.41 g/l $MgCl_2 \cdot 6H_2O$, 10 mg/l $FeSO_{4.7}H_2O$, 2 mg/l $MnSO_4 \cdot 6H_2O$, 0.9 mg/l $ZnSO_4 \cdot 7H_2O$, 0.04 mg/l $(NH_4)6Mo_7O_{24} \cdot 4H_2O$, 30 µg/l biotin, 2 mg/l thiamine hydrochloride, 135 g/l disodium succinate and 30 g/l polyvinyl pyrrolidone having an average molecular weight of 10,000, pH 7.6] containing 1 mg/ml lysozyme. The suspension was transferred into an L-type test tube and gently shaken at 30° C. for 5 hours to prepare protoplasts.

Then, 0.5 ml of the protoplast suspension was taken in a small test tube and centrifuged at 2,500×g for 5 minutes to separate the protoplasts. The protoplasts were suspended in 1 ml of TSMC buffer solution (10 mM $MgCl_2$, 30 mM $CaCl_2$, 50 mM Tris and 400 mM sucrose, pH 7.5) and washed by centrifugation. The protoplasts were resuspended in 0.1 ml of TSMC buffer solution. Then, 100 µl of a 1:1 mixture of TSMC buffer solution at a two-fold concentration and the ligase reaction mixture obtained above was added to the protoplast suspension, and the resulting mixture was further admixed with 0.8 ml of TSMC buffer solution containing 20% PEG 6000. After three minutes, 2 ml of RCGP medium (pH 7.2) was added thereto, and the resulting mixture was centrifuged at 2,500×g for 5 minutes to remove a supernatant. The precipitated protoplasts were suspended in 1 ml of RCGP medium, and 0.2 ml of the suspension was spread on RCGP agar medium (RCGP medium containing 1.4% agar, pH 7.2) containing 400 μg/ml spectinomycin and cultured at 30° C. for 10 days.

Several colonies grown on RCGP agar medium were picked up, and plasmid DNAs were isolated from them as follows. Each of the colonies was inoculated into SSM medium, and cultured with shaking at 30° C. until OD reached 0.2. Penicillin G was added to the culture medium to a concentration of 0.5 unit/ml, and culturing was further continued until OD reached 0.6. Plasmid DNAs were isolated from the cultured cells by the alkali method (Molecular Cloning, p.368).

Digestion with restriction enzymes and analysis by agarose gel electrophoresis revealed that one of the plasmid DNAs thus isolated was composed of a partially digested product (PstI-SstI) of pCG11 and PstI-SstI linker of M13mp19RF DNA (refer to FIG. 1). The plasmid was named pCG111. This plasmid is a very useful plasmid because it has KpnI, SmaI, BamHI, XbaI, SalI and PstI cleavage sites derived from M13mp19 multilinker and is digested only at one site by each of these restriction enzymes.

Figure 2:
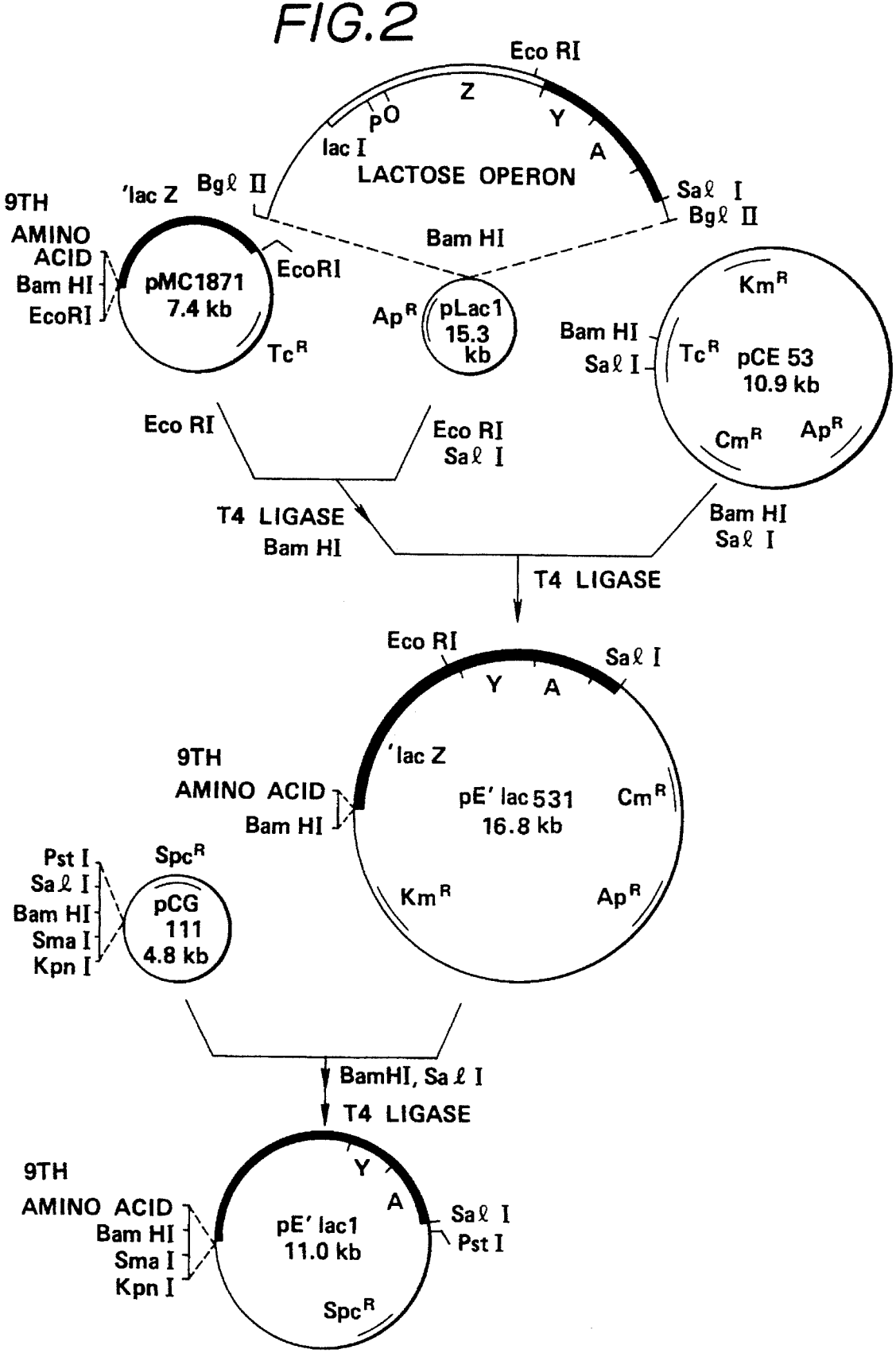
FIG. 2 illustrates the steps for constructing pE'lacl, in which the solid box represents the DNA fragment derived from *Escherichia coli* lactose operon.

(3) Preparation of vector plasmid pE'lacl for the cloning of the region responsible for the initiation of transcription and translation in coryneform bacteria Vector plasmed pE'lacl for the cloning of the region responsible for the initiation of transcription and translation in coryneform bacteria was constructed by the following method using plasmid pLacl containing *Escherichia coli* lactose operon cloned in (1) above, vector plasmid pCG111 prepared in (2) above and pMC1871 (refer to FIG. 2).

pMC1871 commercially available from Pharmacia Fine Chemicals was used in this experiment. Four units of restriction enzyme EcoRI (a product of Takara Shuzo Co., Ltd.) was added to 50 μl of reaction buffer solution for EcoRI (10 mM Tris, 10 mM MgCl$_2$, 100 mM NaCl and 1 mM dithiothreitol, pH 7.5) containing 2 μg of pMC1871 plasmid DNA. The mixture was subjected to reaction at 37° C. for 60 minutes. The reaction mixture was subjected to agarose gel electrophoresis, and about 0.4 μg of an EcoRI-cleaved DNA fragment of 3.0 kb was obtained by the method of Girvitz, et al. (Molecular Cloning p. 168 ).

Separately, 8 units of EcoRI was added to 50 μl of reaction buffer solution for EcoRI containing 4 μg of pLacl plasmid DNA prepared in (1) above, and the mixture was subjected to reaction at 37° C. for 60 minutes. Then, 5 μl of 1M NaCl and 8 units of restriction enzyme SalI (a product of Takara Shuzo Co., Ltd.) were added thereto, and the reaction was continued at 37° C. for an additional 60 minutes. About 0.4 μg of an EcoRI-SalI-cleaved DNA fragment of 3.2 kb was obtained from the reaction mixture by the same method as described above. It is evident from the cleavage map of lactose operon [Experiments with Gene Fusions by T. J. Silhavy, et al.; Cold Spring Harbor Laboratory (1984)] that this DNA fragment contains the structural gene lacy of *Escherichia coli*.

Each of the two DNA fragments obtained above was dissolved in 45 μl of TES buffer solution, and the two solutions were mixed. Then, 10 μl of buffer solution for T4 ligase at a 10-fold concentration, 1 μl of 100 mMATP and 350 units of T4 ligase were added thereto, and the mixture was subjected to ligase reaction at 12° C. for 16 hours. Further, 10 μl of 1M NaCl and 10 units of BamHI were added thereto, and the mixture was subjected to reaction at 37° C. for 60 minutes. The reaction was stopped by heating the reaction mixture at 65° C. for 10 minutes.

Separately, shuttle vector 'pCE53 autonomously replicable in both *Escherichia coli* and *Corynbacterium glutamicum* [Mol. Gen. Genet., 196,175 (1984)] was isolated from *Escherichia coli* K12 strain carrying pCE53 by the method of Ann, et al. To 60 μl of reaction buffer solution for BamHI containing 1 μg of pCE53 plasmid DNA, was added 2 units of BamHI, and the mixture was subjected to reaction at 37° C. for 60 minutes. Then, 6 μl of 1M Nacl and 2 units of SalI were added thereto, and the reaction was continued at 37° C. for 60 minutes and then stopped by heating the reaction mixture at 65° C. for 10 minutes.

Both reaction mixtures obtained above were mixed. Then, 20 μl of buffer solution for T4 ligase at a 10-fold concentration, 2 μl of 100 mMATP and 350 units of T4 ligase were added thereto, and the mixture was subjected to ligase reaction at 12° C. for 16 hours. The ligase reaction mixture thus obtained was used for the transformation of *Escherichia coli* K294 strain according to the method of Dagert, et al., using L-agar medium containing 20 μg/ml kanamycin as a selection medium. From the kanamycin-resistant strains thus obtained, were selected the strains which did not grow on L-agar medium containing 25 μg/ml tetracycline. Plasmids were isolated from these kanamycin-resistant and tetracycline-sensitive strains by the alkali method, and were digested with restriction enzymes, followed by analysis by agarose gel electrophoresis. It was found that one of these plasmids was a plasmid DNA having a size of 16.8 kb as shown in FIG. 2, which was named pE'lac531.

*Corynbacterium glutamicum* ATCC 31833 was transformed with 1 μg of pE'lac531 prepared above in the same manner as in (2). RCGP agar medium containing 200 μg/ml kanamycin was employed as a selection medium, and a plasmid DNA was isolated from the transformant by the alkali method. The plasmid thus isolated was confirmed to be the same plasmid as pE'lac531 by digestion analysis with restriction enzymes. The plasmid pE'lac531 thus obtained (1 μg) and 1 μg of pCG111 prepared in (2) above were dissolved in 80 μl of reaction buffer solution for BamHI. Four units of BamHI was added thereto, and the mixture was subjected to reaction at 37° C. for 60 minutes. Then, 10 μl of 1M NaCl and 4 units of SalI were added thereto, and the reaction was continued at 37° C. for 60 minutes and then stopped by heating at 65° C. for 10 minutes. 10 μl of buffer solution for T4 ligase at a 10-fold concentration, 1 μl of 100 mMATP and 350 units of T4 ligase were further added, and the mixture was subjected to ligase reaction at 12° C. for 16 hours. The ligase reaction mixture thus obtained was used for the transformation of *Corynbacterium glutamicum* ATCC 31833 in the same manner as in (2) above, using RCGP agar medium containing 400 μg/ml spectinomycin as a selection medium.

Plasmids were isolated from the thus obtained spectinomycin-resistant transformants by the alkali method. The plasmids thus obtained were digested with restriction enzymes, and analyzed by agarose gel electrophoresis. It was found that one of the transformants carried a plasmid having a size of 11 kb as shown in FIG. 2. The plasmid, named pE'lacl, carries the replication origin and spectinomycin-resistance gene obtained from plasmids pCG1 and pCG4, respectively, the structural genes for *Escherichia coli* lactose operon in which promoter and eight amino acids on N-terminal side of lacZ are deleted, and BamHI, SmaI and KpnI cleavage sites positioned upstream of said structural genes.

(4) Cloning of a DNA fragment responsible for the initiation of transcription and translation in coryneform bacteria and construction of a recombinant plasmid which confers the ability to assimilate lactose on coryneform bacteria A DNA fragment responsible for the initiation of transcription and translation derived from the chromosomal DNA of Corynbacterium glutamicum ATCC 31833 was cloned by using pE'lacI prepared in (3) above.

The chromosomal DNA of Corynbacterium glutamicum ATCC 31833 was prepared in the following manner.

A seed culture of Corynbacterium glutamicum ATCC 31833 cultured in NB medium was inoculated into 400 ml of SSM medium, and shaking culture was carried out at 30° C. When OD reached 0.2, penicillin G was added to the culture medium to a concentration of 0.5 unit/ml, and culturing was continued until OD reached 0.6.

The cells collected from the culture broth were washed with TES buffer solution, suspended in 10 ml of a lysozyme solution, and subjected to reaction at 37° C. for 4 hours. Then, chromosomal DNA was isolated from the collected cells by the method of Saito and Miura [Biochim. Biophys. Acta, 72, 619 (1963)].

The chromosomal DNA thus obtained was partially digested with restriction enzyme Sau3A. That is, to 90 µl of reaction buffer solution for Sau3A (50 mM Tris, 10 mM $MgCl_2$, 100 mM NaCl and 1 mM dithiothreitol, pH 7.5) containing 2 µg of the chromosomal DNA, was added 0.5 unit of Sau3A (a product of Takara Shuzo Co., Ltd.). The mixture was subjected to reaction at 37° C. for 30 minutes, and the reaction was stopped by heating at 65° C. for 10 minutes.

Separately, 2 units of restriction enzyme BamHI was added to 90 µl of reaction buffer solution for BamHI containing 1 µg of vector pE'lacI DNA. The mixture was subjected to reaction at 37° C. for 60 minutes to completely digest the plasmid, and the reaction was stopped by heating at 65° C. for 10 minutes. Both reaction mixtures obtained above were mixed, and 20 µl of buffer solution for T4 ligase at a 10-fold concentration, 2 µl of 100 mM ATP and 350 units of T4 ligase were added thereto. The mixture was subjected to ligase reaction at 12° C. for 16 hours. The reaction mixture thus obtained was used for the transformation of Corynbacterium glutamicum ATCC 31833 in the same manner as in (2) above, using RCGP agar medium containing 400 µg/ml spectinomycin and 40 µg/ml X-GAL as a selection medium. After culturing at 30° C. for 7 days, several blue-colored colonies were collected, and plasmids were isolated from these strains by the alkali method. Digestion with restriction enzymes and analysis by agarose gel electrophoresis revealed that the DNA fragment derived from the chromosomal DNA of Corynebacterium glutamicum ATCC 31833 was inserted into pE'lacI at the BamHI cleavage site. These plasmids were named pCPL1 to pCPL15. Of these, pCPL7 was found to be a plasmid containing a DNA fragment of 3.1 kb. The strain carrying pCPL7 has been deposited as Corynbacterium glutamicum K74 (FERMBP-1179).

(5) Evaluation of cloned promoter

The degree of β-D-galactosidase expression in Corynbacterium glutamicum ATCC 31833 strains carrying plasmids pCPL1 to pCPL15 respectively obtained in (4) above was examined in the following manner. The cells of each strain cultured in 40 ml of NB medium containing 100 µg/ml spectinomycin were collected, suspended in 50 mM Tris-HCl buffer solution (pH 7.0), and disrupted by ultrasonic treatment under ice cooling for 20. minutes. The disrupted cell suspension was centrifuged to recover a cell extract as the supernatant, which was used to measure the activity of intracellular β-D-galactosidase and the β-D-galactosidase content in intracellular proteins. The β-D-galactosidase activity was determined by the method using o-nitrophenyl-β-D-galactoside (ONPG) [J. H. Miller, "Experiments in Molecular Genetics", p.403 (1972)]. The protein content of the cell extract was measured by using Bio-Rad's assay kit. Table 1 shows the specific activity of intracellullar β-D-galactosidase in Corynebacterium glutamicum ATCC 31833 strains carrying plasmids pCPL1 to pCPL15 and vector pE'lacI respectively.

At the same time, the pattern of intracellular proteins in these strains was investigated through SDS-polyacrylamide gel electrophoresis [Laemmli, Nature, 227, 680 (1980)]. A protein band which was not found with the strain carrying vector pE'lacI was observed with the strains carrying pCPL1 to pCPL15. The positions of these bands were nearly the same as that of β-D-galactosidase and intensity of the protein bands corresponded to the level of the intracellular β-D-galactosidase activities shown in Table 1.

The results obtained above clearly show that DNA fragments containing the region responsible for the initiation of transcription and translation derived from a strain of the genus Corynbacterium or Brevibacterium can be prepared by using vector pE'lacI of the present invention.

TABLE 1

| Strain | Specific Activity (U/mg) |
|---|---|
| Corynebacterium glutamicum ATCC 31833/pCPL1 | 2200 |
| Corynebacterium glutamicum ATCC 31833/pCPL2 | 2100 |
| Corynebacterium glutamicum ATCC 31833/pCPL3 | 2900 |
| Corynebacterium glutamicum ATCC 31833/pCPL4 | 3200 |
| Corynebacterium glutamicum ATCC 31833/pCPL5 | 880 |
| Corynebacterium glutamicum ATCC 31833/pCPL6 | 1000 |
| Corynebacterium glutamicum ATCC 31833/pCPL7 | 3000 |
| Corynebacterium glutamicum ATCC 31833/pCPL8 | 1100 |
| Corynebacterium glutamicum ATCC 31833/pCPL9 | 76 |
| Corynebacterium glutamicum ATCC 31833/pCPL10 | 2500 |
| Corynebacterium glutamicum ATCC 31833/pCPL11 | 7600 |
| Corynebacterium glutamicum ATCC 31833/pCPL12 | 1400 |
| Corynebacterium glutamicum ATCC 31833/pCPL13 | 1100 |
| Corynebacterium glutamicum ATCC 31833/pCPL14 | 550 |
| Corynebacterium glutamicum ATCC 31833/pCPL15 | 81 |
| Corynebacterium glutamicum ATCC 31833/pE'lacl | <1 |

(6) Gene expression in Escherichia coli by using the region responsible for the initiation of transcription and translation derived from a strain of the genus Corynbacterium or Brevibacterium Shuttle plasmids for Escherichia coli and coryneform bacteria were constructed by inserting plasmid vector pACYC177 Chang, et al., J. Bacteriol, 134, 1141 (1978)], which is autonomously replicable in Escherichia coli and has kanamycin-and ampicillin-resistance markers, into pE'lacI and each of the plasmids pCPL3, 10, 12 and 14 obtained in (4) above at the PstI cleavage site. The shuttle plasmids were introduced into Escherichia coli to examine the degree of expression of the gene coding for β-D-galactosidase therein.

One unit of restriction enzyme PstI (a product of Takara Shuzo Co., Ltd.) was added to 45 µl of reaction buffer solutions for PstI (10 mM Tris, 10 mM $MgCl_2$, 100 mM NaCl and 1 mM dithiothreitol, pH 7.5) containing 0.5 µg of pE'lacI, pCPL3, pCPL10, pCPL12 and pCPL14, respectively. The mixture was subjected to reaction at 37° C. for 60 minutes, and the reaction was stopped by heating at 65° C. for 10 minutes.

Separately, 6 units of PstI was added to 225 µl of reaction buffer solution for PstI containing 2.5 µg of plasmid pACYC177, and the reaction was allowed to proceed and stopped in the same manner as above.

Forty-five μl each of both reaction mixtures obtained above were mixed, and 10 μl of buffer solution for T4 ligase at a 10-fold concentration, 1 μl of 100 mM ATP and 350 units of T4 ligase were added thereto. The mixture was subjected to ligase reaction at 12° C. for 16 hours. The ligase reaction mixture thus obtained was used for the transformation of *Escherichia coli* K72 derived from *Escherichia coli* K12 strain, in the same manner as in (1) above, using L-agar medium containing 100 μg/ml spectinomycin and 20 μg/ml kanamycin as a selection medium. The colonies grown on the agar medium were picked up, and plasmids were isolated from the transformants by the method of Ann, et al. The plasmid DNAs thus obtained were digested with restriction enzymes, and analyzed by agarose gel electrophoresis. It was confirmed that the plasmids had structures wherein pACYC177 DNA fragment of 3.6 kb was inserted into pE'lacI and plasmids pCPL3, 10, 12 and 14, respectively, at the PstI cleavage site. These plasmids were named pCPL103, 110, 112, 114 and pE'lac101, respectively. Each of these plasmids was used for the transformation of *Corynbacterium glutamicum* ATCC 31833 in the same manner as in (2) above to obtain a spectinomycin- and kanamycin-resistant transformant. *Corynbacterium glutamicum* ATCC 31833 and *Escherichia coli* K72 strains carrying pE'lac101 and pCPL103, 110, 112 and 114 obtained above, respectively, were examined for the specific activity of intracellular β-D-galactesidase by the same method as in (5) above, except that the ultrasonic treatment was carried out for 2 minutes for the transformants of K72 strain. The results are shown in Table 2.

TABLE 2

| Strain | Specific Activity (U/mg) |
| --- | --- |
| *Corynebacterium glutamicum* ATCC 31833/pCPL103 | 10,000 |
| *Corynebacterium glutamicum* ATCC 31833/pCPL110 | 440 |
| *Corynebacterium glutamicum* ATCC 31833/pCPL112 | 1,500 |
| *Corynebacterium glutamicum* ATCC 31833/pCPL114 | 570 |
| *Corynebacterium glutamicum* ATCC 31833/pE'lac101 | <1 |
| *Escherichia coli* K72/pCPL103 | 9 |
| *Escherichia coli* K72/pCPL110 | 30 |
| *Escherichia coli* K72/pCPL112 | 11 |
| *Escherichia coli* K72/pCPL114 | 21 |
| *Escherichia coli* K72/pE'lac101 | <1 |

As shown in Table 2, gene expression using the region responsible for the initiation of transcription and translation derived from *Corynbacterium glutamicum* in *Escherichia coli* is feeble and has no correlation with that in *Corynbacterium glutamicum*. This fact indicates that there is a difference in nature between the region responsible for the initiation of transcription and translation in strains of the genus *Corynbacterium* or *Brevibacterium* and the promoter and ribosome-binding sequence in *Escherichia coli*.

(7) Conferment of the ability to assimilate lactose on strains of the genus *Corynbacterium* or *Brevbacterium* by introduction of pCPL7 *Corynbacterium glutamicum* ATCC 31833,

*Corynbacterium herculis* is ATCC 13868, *Brevibacterium flavum* ATCC 14067 and *Brevibacterium lactofermentum* ATCC 13869 were transformed by using 1 μg of pCPL7 according to the same method as in (4) above. It was confirmed that plasmids isolated from the spectinomycin-resistant transformants which formed blue-colored colonies were identical with pCPL7.

A culture test of the transformants obtained above and their parent strains in a medium containing lactose as a carbon source was carried out in the following manner. Each strain was cultured with shaking in NB medium at 30° C. for 24 hours. For the culture of the transformants, spectinomycin was added to NB medium at a concentration of 100 μg/ml. Then, the cells recovered from 0.5 ml of the seed culture broth were washed with physiological saline solution by centrifugation and then inoculated into 10 ml of a minimal medium containing lactose as a carbon source [10 g/l lactose, 10 g/l $(NH_4)_2SO_4$, 1 g/l $KH_2PO_4$, 0.4 g/l $MgSO_4 \cdot 7H_2O$, 2 mg/l $FeSO_4 \cdot 7H_2O$, 2 mg/l $MnSO_4 \cdot 4H_2O$, 60 μg/l biotin, 2 mg/l thiamine hydrochloride, 3 g/l urea and 50 mg/l NaCl, pH 7.2] in an L-type test tube. Culturing was carried out with shaking at 30° C. for 12 hours, and turbidity at 660 nm was measured. The results are shown in Table 3.

TABLE 3

| Strain | | $\Delta OD_{660}$ |
| --- | --- | --- |
| *Corynebacterium glutamicum* | ATCC 31833 | 0.05 |
| *Corynebacterium glutamicum* | ATCC 31833/pCPL7 | 0.72 |
| *Corynebacterium herculis* | ATCC 13868 | 0.03 |
| *Corynebacterium herculis* | ATCC 13868/pCPL7 | 0.65 |
| *Brevibacterium flavum* | ATCC 14067 | 0.04 |
| *Brevibacterium flavum* | ATCC 14067/pCPL7 | 0.70 |
| *Brevibacterium lactofermentum* | ATCC 13869 | 0.03 |
| *Brevibacterium lactofermentum* | ATCC 13869/pCPL7 | 0.64 |

As can be seen from Table 3, this test showed that the transformants carrying pCPL7 acquired the ability to assimilate lactose.

(8) Production of glutamic acid from lactose-containing materials (A) Glutamic acid production test on *Corynbacterium glutamicum* ATCC 31833, *Corynbacterium herculis* ATCC 13868, *Brevibacterium flavum* ATCC 14067 and *Brevibacterium lactofermentum* ATCC 13869 each carrying pCPL7 and prepared in (7) above and their parent strains was carried out in the following manner:

Each strain was inoculated into a seed culture medium (pH 7.2) comprising 40 g/l glucose, 20 g/l polypeptone, 1.5 g/l $KH_2PO_4$, 0.5 g/l $K_2HPO_4$, 0.5 g/l $MgSO_4 \cdot 7H_2O$, 10 μg/l biotin and 3 g/l urea, and cultured with shaking at 30° C. for 24 hours. For the culture of the transformants, spectinomycin was added to a seed culture medium at a concentration of 100 g/ml. Then, 4 ml of the seed culture was inoculated into 20 ml of a production medium (pH 6.5) comprising 100 g/l lactose, 2 g/l $(NH_4)_2SO_4$, 1.0 g/l $KH_2PO_4$, 0.5 g/l $K_2HPO_4$, 0.5 g/l $MgSO_4 \cdot 7H_2O$, 1 mg/l thiamine hydrochloride, 2 mg/l $FeSO_4 \cdot 7H_2O$, 10 mg/l $MnSO_4 \cdot 4H_2O$, 1 mg/l $CuSO_4 \cdot 5H_2O$, 5 g/l urea and 10 mg/l Phenol Red in a 300 ml-Erlenmeyer flask. Shaking culture was carried out at 30° C. for 30 hours, and 1 ml of 10% urea solution was added 12 hours and 20 hours after the start of culturing to maintain the pH of the culture broth within the range of 6.0 to 8.0. After the culturing was finished, the culture filtrate was subjected to paper chromatography and the amount of L-glutamic acid formed was determined colorimetrically by using the color development with ninhydrin. The results are shown in Table 4.

TABLE 4

| Strain | | L-Glutamic acid (g/l) |
|---|---|---|
| Corynebacterium glutamicum | ATCC 31833 | 0.7 |
| Corynebacterium glutamicum | ATCC 31833/pCPL7 | 17.3 |
| Corynebacterium herculis | ATCC 13868 | 0.5 |
| Corynebacterium herculis | ATCC 13868/pCPL7 | 11.4 |
| Brevibacterium flavum | ATCC 14067 | 0.5 |
| Brevibacterium flavum | ATCC 14067/pCPL7 | 14.6 |
| Brevibacterium lactofermentum | ATCC 13869 | 0.4 |
| Brevibacterium lactofermentum | ATCC 13869/pCPL7 | 13.4 |

(B) Glutamic acid production test on the same strains as used in (A) was carried out in the same manner as in (A), except that whey powder (lactose content: 75%) was used in place of lactose in the production medium in an amount corresponding to 10% lactose, that 5 units/ml penicillin G was added when the seed culture was inoculated, and that shaking culture was carried out at 30° C. for 72 hours. The amounts of L-glutamic acid determined in the same manner as in (A) are shown in Table 5.

TABLE 5

| Strain | | L-Glutamic acid (g/l) |
|---|---|---|
| Corynebacterium glutamicum | ATCC 31833 | 0.6 |
| Corynebacterium glutamicum | ATCC 31833/pCPL7 | 15.9 |
| Corynebacterium herculis | ATCC 13868 | 0.5 |
| Corynebacterium herculis | ATCC 13868/pCPL7 | 10.2 |
| Brevibacterium flavum | ATCC 14067 | 0.4 |
| Brevibacterium flavum | ATCC 14067/pCPL7 | 13.7 |
| Brevibacterium lactofermentum | ATCC 13869 | 0.4 |
| Brevibacterium lactofermentum | ATCC 13869/pCPL7 | 12.8 |

(9) Production of glutamine from lactose-containing material

Corynbacterium glutamicum ATCC 13761 was transformed with pCPL7 by the same method as in (7) above, and it was cofirmed that the transformant thus obtained carried pCPL7.

Glutamine production test on the transformant and the parent strain was carried out in the following manner:

Each strain was inoculated into a seed culture medium (pH 7.2) comprising 50 g/l glucose, 5 g/l (NH$_4$)2SO$_4$, 3 g/l urea, 2 g/l corn steep liquor, 2 g/l meat extract, 0.5 g/l KH$_2$PO$_4$, 1.5 g/l K$_2$HPO$_4$, 0.5 g/l MgSO$_4$, 0.02 g/l FeSO$_4$·7H$_2$O, 0.02 g/l MnSO$_4$·7H$_2$O, 20 µg/l biotin and 1 mg/l thiamine hydrochloride, and cultured with shaking at 28° C. for 24 hours. For the culture of the transformant, spectinomycin was added to a seed culture medium at a concentration of 100 µg/ml. Then, 1 ml of the seed culture was inoculated into 20 ml of a production medium (pH 6.8) comprising 120 g/l lactose, 40 g/l (NH$_4$)$_2$SO$_4$, 5 g/l urea, 0.5 g/l KH$_2$PO$_4$, 0.5 g/l K$_2$HPO$_4$, 0.5 g/l MgSO$_4$·7H$_2$O, 0.02 g/l FeSO$_4$·7H$_2$O, 0.01 g/l MnSO$_4$·7H$_2$O, 3.5 µg/l biotin, 1 mg/l thiamine hydrochloride and 20 g/l CaCO$_3$ in a 300 ml-Erlenmeyer flask. Shaking culture was carried out at 30° C. for 72 hours. After the culturing was finished, the culture filtrate was subjected to paper chromatography and the amount of L-glutamine formed was determined colorimetrically by using the color development with ninhydrin. The results are shown in Table 6.

TABLE 9

| Strain | | L-Glutamic acid (g/l) |
|---|---|---|
| Corynebacterium glutamicum | ATCC 13761 | 0.1 |
| Corynebacterium glutamicum | ATCC 13761/pCPL7 | 3.7 |

(10) Production of lysine from lactose-containing materials (A) Corynbacterium glutamicum RH6 (FERM BP-704) (homoserine-requiring), Brevibacterium flavum ATCC 21528 (thialysine-resistant) and Brevibacterium lactofermentum ATCC 21086 (threonine-, isoleucine- and valine-requiring) were each transformed with pCPL7 by the same method as in (7) above, and it was confirmed that the transformants .thus obtained carried pCPL7.

Lysine production test on the transformants and their parent strains was carried out in the following manner:

Each strain was cultured in NB medium at 30° C. for 16 hours. For the culture of the transformants, spectinomycin was added to NB medium at a concentration of 100 µg/ml. Then, 0.5 ml of the seed culture was inoculated into 5 ml of a production medium (pH 7.2) comprising 100 g/l lactose, 30 g/l (NH$_4$)2SO$_4$, 0.5 g/l KH$_2$PO$_4$, 0.5 g/l K$_2$HPO$_4$, 1 g/l MgSO$_4$·7H$_2$O, 10 mg/l FeSO$_4$·7H$_2$O, 10 mg/l MnSO$_4$·7H$_2$O, 100 µg/l biotin and 30 g/l CaCO$_3$ in a test tube. Homoserine (100 µg/ml) was further added to the production medium for RH6 strain and its transformant, and 100 µg/ml each of threonine, isoleucine and valine were added to the production medium for ATCC 21086 strain and its transformant. Shaking culture was carried out at 30° C. for 72 hours. After the culturing was finished, the amount of L-lysine formed was colorimetrically determined by the acidic copper ninhydrin method [Chinard, J. Biol. Chem., 199, 91 (1952)]. The results are shown in Table 7.

TABLE 7

| Strain | | L-Lysine (g/l) |
|---|---|---|
| Corynebacterium glutamicum | RH6 (FERM BP-704) | 0.4 |
| Corynebacterium glutamicum | RH6/pCPL7 | 7.2 |
| Brevibacterium flavum | ATCC 21528 | 0.3 |
| Brevibacterium flavum | ATCC 21528/pCPL7 | 4.8 |
| Brevibacterium lactofermentum | ATCC 21086 | 0.3 |
| Brevibacterium lactofermentum | ATCC 21086/pCPL7 | 5.2 |

(B) Lysine production test on the same strains as used in (A) was carried out in the same manner as in (A), except that whey powder was used in place of lactose in the production medium in an amount corresponding to 100 g/l lactose. The results are shown in Table 8.

TABLE 7

| Strain | | L-Lysine (g/l) |
|---|---|---|
| Corynebacterium glutamicum | RH6 (FERM BP-704) | 0.3 |
| Corynebacterium glutamicum | RH6/pCPL7 | 5.5 |
| Brevibacterium flavum | ATCC 21528 | 0.2 |
| Brevibacterium flavum | ATCC 21528/pCPL7 | 3.6 |
| Brevibacterium lactofermentum | ATCC 21086 | 0.3 |
| Brevibacterium lactofermentum | ATCC 21086/pCPL7 | 3.8 |

(11) Production of threonine from lactose-containing materials (A) *Corynbacterium glutamicum* ATCC 21660 (methionine-requiring, and resistant to thialysine and α-amino-β-hydroxyvaleric acid) was transformed with pCPL7 by the same method as in (7) above, and it was confirmed that the transformant thus obtained carried pCPL7.

Threonine production test on the transformant and the parent strain was carried out in the following manner:

Each strain was cultured with shaking in NB medium at 30° C. for 24 hours. For the culture of the transformant, spectinomycin was added to NB medium at a concentration of 100 μg/ml. Then, 0.5 ml of the seed culture was inoculated into 5 ml of a production medium (pH 7.2) comprising 100 g/l lactose, 20 g/l $(NH_4)_2SO_4$, 0.5 g/l $KH_2PO_4$ 0.5 g/l $K_2HPO_4$, 1 g/l $MgSO_4 \cdot 7H_2O$, 10 mg/R $FeSO_4 \cdot 7H_2O$, 10 mg/l $MnSO_4 \cdot 7H_2O$, 100 μg/l biotin, 20 g/l $CaCO_3$ and 50 mg/l methionine in a test tube. Shaking culture was carried out at 30° C. for 82 hours. After the culturing was finished, the culture filtrate was subjected to paper chromatography and the amount of L-threonine formed was determined colorimetrically by using the color development with ninhydrin. The results are shown in Table 9.

TABLE 9

| Strain | | L-Threonine (g/l) |
|---|---|---|
| *Corynebacterium glutamicum* | ATCC 21660 | 0.1 |
| *Corynebacterium glutamicum* | ATCC 21660/pCPL7 | 3.0 |

(B) Threonine production test on the same strains as used in (A) was carried out in the same manner as in (A), except that whey powder was used in place of lactose in the production medium in an amount corresponding to 100 g/l lactose. The results are shown in Table 10.

TABLE 10

| Strain | | L-Threonine (g/l) |
|---|---|---|
| *Corynebacterium glutamicum* | ATCC 21660 | 0.1 |
| *Corynebacterium glutamicum* | ATCC 21660/pCPL7 | 2.5 |

(12) Production of isoleucine from lactose-containing material

*Corynbacterium glutamicum* N-222 (KY 10589) (FERM P-2843) (lysine-requiring and thiaisoleucine-resistant) was transformed with pCPL7 by the same method as in (7) above, and it was confirmed that the transformant thus obtained carried pCPL7.

Isoleucine production test on the transformant and the parent strain was carried out in the following manner:

Each strain was cultured with shaking in a seed medium (pH 7.4) comprising 20 g/l glucose, 10 g/l peptone, 10 g/l yeast extract and 2.5 g/l NaCl at 30° C. for 24 hours. For the culture of the transformant, spectinomycin was added to a seed medium at a concentration of 100 μg/ml. Then, 2 ml of the seed culture was inoculated into 20 ml of a production medium (pH 7.4) compirisng 100 g/l (as lactose) whey powder, 50 g/l $(NH_4)_2SO_4$, 1 g/l $MgSO_4 \cdot 7H_2O$, 0.5 g/l $KH_2PO_4$, 0.5 g/l $K_2HPO_4$, 0.01 g/l $FeSO_4 \cdot 7H_2O$, 0.01 g/l $MnSO_4 \cdot 4H_2O$, 100 μg/l biotin, 100 mg/l lysine hydrochloride and 20 g/l $CaCO_3$ in a 300 ml-Erlenmeyer flask. Shaking culture was carried out at 30° C. for 96 hours. After the culturing was finished, the culture filtrate was subjected to paper chromatography and the amount of L-isoleucine formed was determined colorimetrically by using the color development with ninhydrin. The results are shown in Table 11.

TABLE 11

| Strain | L-Isoleucine (g/l) |
|---|---|
| *Corynebacterium glutamicum* N-222 (KY-10589) (FERM P-2843) | 0.1 |
| *Corynebacterium glutamicum* N-222/pCPL7 | 5.1 |

(13) Production of valine from lactose-containing material

*Brevibacterium lactofermentum* KY 10614 (FERM P-2925) (thialysine-resistant) was transformed with pCPL7 by the same method as in (7) above, and it was confirmed that the transformant thus obtained carried pCPL7.

Valine production test on the transformant and the parent strain was carried out in the following manner:

Each strain was cultured in a seed medium (pH 7.2) comprising 50 g/l glucose, 10 g/l peptone, 10 g/l yeast extract, 2.5 g/l NaCl, 3 g/l urea, 50 μg/l biotin and 5 g/l corn steep liquor at 28° C. for 24 hours. For the culture of the transformant, spectinomycin was added to a seed medium at a concentration of 100 μg/ml. Then, 2 ml of the seed culture was inoculated into 20 ml of a production medium (pH 6.8) comprising 100 g/l (as lactose) whey powder, 20 g/l $(NH_4)_2SO_4$, 0.5 g/l $MgSO_4 \cdot 7H_2O$, 2 g/l $KH_2PO_4$, 0.01 g/l $FeSO_4 \cdot 7H_2O$, 0.01 g/l $MnSO_4 \cdot 4H_2O$, 50 μg/l biotin and 30 g/l $CaCO_3$ in a 300 ml-Erlenmeyer flask. Shaking culture was carried out at 28° C. for 72 hours. After the culturing was finished, the culture filtrate was subjected to paper chromatography and the amount of L-valine formed was determined colorimetrically by using the color development with ninhydrin. The results are shown in Table 12.

TABLE 12

| Strain | L-Valine (g/l) |
|---|---|
| *Brevibacterium lactofermentum* KY-10614 (FERM P-2925) | 0.2 |
| *Brevibacterium lactofermentum* KY-10614/pCPL7 | 7.6 |

(14) Production of leucine from lactose-containing material

*Brevibacterium lactofermentum* ATCC 21888 (FERM P-1837, thialysine-resistant) was transformed with pCPL7 by the same method as in (7) above, and it was confirmed that the transformant thus obtained carried pCPL7.

Leucine production test on the transformant and the parent strain was carried out under the same conditions as in the valine production test described in (13) above. The results are shown in Table 13.

TABLE 13

| Strain | L-Leucine (g/l) |
|---|---|
| *Brevibacterium lactofermentum* ATCC 21888 | 0.1 |
| *Brevibacterium lactofermentum* ATCC 21888/pCPL7 | 4.9 |

(15) Production of tryptophan from lactose-containing materials (A) *Corynbacterium glutamicum* K-55 (FERM BP-864) (phenylalanine-requiring, tyrosine-requiring, and resistant to 5-methyltryptophan, tryptophan hydroxamate, 6-fluorotryptophan, 4-methyltryptophan, p-fluorophenylalanine, p-aminophenylalamine, tyrosine hydroxamate and phenylalanine hydroxamate) was transformed with pCPL7 by the same method as in (7) above, and it was confirmed that the transformant thus obtained carried pCPL7.

Tryptophan production test on the transformant and the parent strain was carried out in the following manner:

Each strain was cultured with shaking in NB medium at 30° C. for 16 hours. For the culture of the transformant, spectinomycin was added to NB medium at a concentration of 100 µg/ml. Then, 0.5 ml of the seed culture was inoculated into 5 ml of a production medium (pH 7.2) comprising 100 g/l lactose, 20 g/l $(NH_4)_2SO_4$, 0.5 g/l $KH_2PO_4$, 0.5 g/l $K_2HPO_4$, 0.25 g/l $MgSO_4 \cdot 7H_2O$, 2.5 g/l NZ-amine and 20 g/l $CaCO_3$ in a test tube. Shaking culture was carried out at 30° C. for 84 hours. After the culturing was finished, the culture filtrate was subjected to paper chromatography and the amount of L-tryptophan formed was determined colorimetrically by using the color development with ninhydrin. The results are shown in Table 14.

TABLE 14

| Strain | L-Tryptophan (g/l) |
| --- | --- |
| Corynebacterium glutamicum K-55 (FERM BP-864) | 0.2 |
| Corynebacterium glutamicum K-55/pCPL7 | 2.8 |

(B) Tryptophan production test on the same strains as used in (A) was carried out in the same manner as in (A), except that whey powder was used in place of lactose in the production medium in an amount corresponding to 100 g/l lactose. The results are shown in Table 15.

TABLE 15

| Strain | L-Tryptophan (g/l) |
| --- | --- |
| Corynebacterium glutamicum K-55 (FERM BP-864) | 0.1 |
| Corynebacterium glutamicum K-55/pCPL7 | 2.4 |

(16) Production of phenylalanine from lactose-containing material

*Corynbacterium glutamicum* K38 (FERM BP-454) (resistant to p-fluorophenylalanine and p-aminophenylalanine) was transformed with pCPL7 by the same method as in (7) above, and it was confirmed that the transformant thus obtained carried pCPL7.

Phenylalanine production test on the transformant and the parent strain was carried out under the same conditions as in the tryptophan production test described in (15)-(B) above. The results are shown in Table 16.

TABLE 16

| Strain | L-Phenylalanine (g/l) |
| --- | --- |
| Corynebacterium glutamicum K38 (FERM BP-454) | 0.1 |
| Corynebacterium glutamicum K38/pCPL7 | 2.8 |

(17) Production of tyrosine from lactose-containing material

*Corynbacterium glutamicum* K43 (FERM BP-457) (resistant to 3-aminotyrosine, p-aminophenylalanine, p-fluorophenylalanine and tyrosine hydroxamate) was transformed with pCPL7 by the same method as in (7) above, and it was confirmed that the transformant thus obtained carried pCPL7.

Tyrosine production test on the transformant and the parent strain was carried out under the same conditions as in the tryptophan production test described in (15)-(B) above. The results are shown in Table 17.

TABLE 17

| Strain | L-Tyrosine (g/l) |
| --- | --- |
| Corynebacterium glutamicum K43 (FERM BP-457) | 0.1 |
| Corynebacterium glutamicum K43/pCPL7 | 2.0 |

(18) Production of histidine from lactose-containing material *Corynbacterium glutamicum* H-d (FERM P-8185) (resistant to 2-thiazolalanine, 6-mercaptoguanine, 8-azaguanine, 6-azauracil, 6-methylpurine, 5-methyltryptophan, streptomycin, gramicidin and p-coumaric acid) was transformed with pCPL7 by the same method as in (7) above, and it was confirmed that the transformant thus obtained carried pCPL7.

Histidine production test on the transformant and the parent strain was carried out in the following manner:

Each strain was cultured with shaking in a seed medium (pH 7.2) comprising 40 g/l. glucose, 20 g/l polypeptone, 1.5 g/l $KH_2PO_4$, 0.5 g/l $K_2HPO_4$, 0.5 g/l $MgSO_4 \cdot 7H_2O$, 50 µg/l biotin, 5 g/l yeast extract, 3 g/l urea and 10 mg/l thiamine hydrochloride at 30° C. for 24 hours. For the culture of the transformant, spectinomycin was added to a seed medium at a concentration of 100 µg/ml. Then, 1 ml of the seed culture was inoculated into 20 ml of a production medium (pH 7.4) comprising 70 g/l (as lactose) whey powder, 5 g/l meat extract, 40 g/l $(NH_4)_2SO_4$, 0.5 g/l $MgSO_4 \cdot 7H_2O$, 1.5 g/l $KH_2PO_4$, 0.5 g/l $K_2HPO_4$, 3 g/l urea, 2.5 g/l NaCl, 10 mg/l $FeSO_4 \cdot 7H_2O$, 10 mg/l $MnSO_4 \cdot 4H_2O$, 2 mg/l $CuSO_4$, 1 mg/l $ZnSO_4$, 100 µg/l biotin, 10 mg/l thiamine hydrochloride, 10 mg/l β-alanine, 10 mg/l nicotinic acid, 10 mg/l calcium pantothenate and 30 g/l $CaCO_3$ in a 300 ml-Erlenmeyer flask. Shaking culture was carried out at 30° C. for 84 hours. After the culturing was finished, the culture filtrate was subjected to paper chromatography and the amount of L-histidine formed was determined colorimetrically with Pauly's reagent by using the color development with ninhydrin [Agric. Biol. Chem., 38., 189 (1974)]. The results are shown in Table 18.

TABLE 18

| Strain | L-Histidine (g/l) |
| --- | --- |
| Corynebacterium glutamicum H-d (FERM P-8185) | 0.4 |
| Corynebacterium glutamicum H-d/pCPL7 | 6.7 |

(19) Production of arginine from lactose-containing material

Arginine production test from a lactose-containing material was carried out by using *Corynbacterium glutamicum* ATCC 31833 carrying pCPL7 and plasmid pEarg5 containing the genes responsible for arginine-synthesis.

The plasmid pEarg5 was prepared from plasmid pEarg1 (Japanese published Unexamined Patent Application No. 66989/85) containing genes responsible for arginine-synthesis, argECBH genes derived from *Escherichia coli* according to the procedure described below.

Plasmid pEarg1 DNA was isolated from *Corynbacterium glutamicum* K46 (FERMBP-356) in the following manner. That is, the strain was cultured with shaking in SSM medium at 30° C. When OD reached 0.2, penicillin G was added to the culture medium to a concentration of 0.5 unit/ml, and the culturing was continued until OD reached 0.6. From the cultured cells thus obtained, pEarg1 plasmid DNA was isolated in the same manner as in (2) above for the isolation of pCG11.

Then, 2 μg of the plasmid DNA thus isolated was dissolved in 20 μl of reaction buffer solution for restriction enzyme SalI (10 mM Tris, 10 mM $MgCl_2$, 150 mM NaCl and 1 mM dithiothreitol, pH 7.5), and 6 units each of PstI and SalI were added thereto. The mixture was subjected to reaction at 37° C. for 60 minutes. The reaction mixture was subjected to agarose gel electrophoresis, and about 0.3 μg of a SalI-PstI-cleaved DNA fragment of 4.0 kb containing argBCH genes was obtained by the method of Girvitz, et al.

Separately, plasmid pCE54 (Japanese Published Unexamined Patent Application No. 105999/83) autonomously replicable in both *Escherichia coli* and strains of the genus *Corynoacterium* was isolated from *Escherichia coli* K12 strain carrying pCE54 by the method of Ann, et al. To 20 μl of reaction buffer solution for SalI containing 5 μg of pCE54 plasmid DNA, was added 6 units of SalI, and the mixture was subjected to reaction at 37° C. for 60 minutes. Further, 2 units of PstI was added thereto, and the mixture was subjected to reaction at 37° C. for 30 minutes. About 1 μg of a SalI-PstI-cleaved DNA fragment of 10.6 kb was isolated from the reaction mixture by the method fo Girvitz, et al.

Both DNA fragments obtained above were dissolved in 180 μl of TES buffer solution, and 20 μl of buffer solution for T4 ligase at a 10-fold concentration, 2 μl of 100 mM ATP and 350 units of T4 ligase were added thereto. The mixture was subjected to ligase reaction at 12° C. for 16 hours. The ligase reaction mixture thus obtained was used for the transformation of *Escherichia coli* K294 by the method of Dagert, et al., using L-agar medium containing 20 μg/ml kanamycin as a selection medium. The colonies grown on the medium were selected. The transformants thus obtained were spread on L-agar medium containing 25 μg/ml chloramphenicol, and the colonies which did not grow thereon were selected. A plasmid was isolated from the transformant thus obtained by the alkali method, and after digestion with restriction enzymes, the plasmid was analyzed by agarose gel electrophoresis. It was found that the plasmid had a structure wherein the DNA fragment of 4.0 kb derived from pEarg1 and the DNA fragment of 10.6 kb derived from pCE54 and containing the kanamycin-resistance gene were joined at their PstI- and SalI-cohesive ends. This plasmid was named pEarg5.

Plasmid pEarg5 DNA thus prepared was used to transform *Corynbacterium glutamicum* ATCC 31833, and arginine production test on the transformant was carried out in the following manner:

The transformation was carried out by the protoplast method described in (2) using RCGP agar medium containing 200 μg/ml kanamycin as a selection medium. The transformant thus obtained was cultured with shaking in NB medium containing 20 μg/ml kanamycin at 30° C. for 16 hours. Then, 0.5 ml of the seed culture was inoculated into 5 ml of a production medium (H 7.0) comprising 80 g/l (as glucose) blackstrap molasses, 40 g/l $(NH_4)_2SO_4$, 0.5 g/l $KH_2PO_4$, 0.5 g/l $K_2HPO_4$ and 20 g/l $CaCO_3$ in a test tube. Shaking culture was carried out at 30° C. for 72 hours. After the culturing was finished, the culture filtrate was subjected to paper chromatography and the amount of L-arginine formed was determined colorimetrically by using the color development with ninhydrin. The amount of L-arginine produced was 1.5 g/l, and thus pEarg5 was confirmed to be capable of conferring the ability to produce arginine on glutamic acid-producing coryneform bacteria.

*Corynbacterium glutamicum* ATCC 31833 carrying pEarg5 was further transformed with pCPL7 by the same method as in (7) above. That is, the transformation was carried out by the protoplast method described in (2) using RCGP agar medium containing 200 μg/ml kanamycin and 400 μg/ml spectinomycin as a selection medium. It was confirmed that the transformant obtained carried both pEarg5 and pCPL7.

Arginine production test on the strain carrying pEarg5 and the strain carrying both pCPL7 and pEarg5 was carried out in the following manner:

Each strain was cultured with shaking in NB medium containing 20 μg/ml kanamycin for the strain carrying pEarg5, and 20 μg/ml kanamycin and 100 μg/ml spectinomycin for the strain carrying both pCPL7 and pEarg5 at 30° C. for 16 hours. Then, 0.5 ml of the seed culture was inoculated into 5 ml of a production medium (pH 7.0) comprising 80 g/l (as lactose) whey powder, 40 g/l $(NH_4)_2SO_4$, 0.5 g/l $KH_2PO_4$, 0.5 g/l $K_2HPO_4$ and 20 g/l $CaCO_3$ in a test tube. Shaking culture was carried out and the amount of L-arginine formed was determined in the same manner as above. The results are shown in Table 19.

TABLE 19

| Strain | L-Arginine (g/l) |
|---|---|
| *Corynebacterium glutamicum* ATCC 31833/pEarg5 | 0.01 |
| *Corynebacterium glutamicum* ATCC 31833/pEarg5, pCPL7 | 0.6 |

(20) Production of ornithine from lactose-containing material

*Corynbacterium glutamicum* ATCC 13232 (arginine-requiring) was transformed with pCPL7 by the same method as in (7) above, and it was confirmed that the transformant thus obtained carried pCPL7.

Ornithine production test on the transformant and the parent strain was carried out in the following manner:

Each strain was cultured with shaking in NB medium at 30° C. for 16 hours. For the culture of the transformant, spectinomycin was added to NB medium at a concentration of 100 μg/ml. Then, 0.5 ml of the seed culture was inoculated into 5 ml of a production medium (pH 7.0) comprising 80 g/l lactose, 40 g/l $(NH_4)_2SO_4$, 0.5 g/l $KH_2PO_4$, 0.5 g/l $K_2HPO_4$, 100 mg/l L-arginine and 20 g/l $CaCO_3$ in a test tube, and shaking culture was carried out at 30° C. for 72 hours. After the culturing was finished, the culture filtrate was subjected to paper chromatography and the amount of L-ornithine formed was determined colorimetrically by using the color development with ninhydrin. The results are shown in Table 20.

TABLE 20

| Strain | L-Ornithine (g/l) |
|---|---|
| *Corynebacterium glutamicum* ATCC 13232 | 0.05 |
| *Corynebacterium glutamicum* ATCC 13232/pCPL7 | 9.2 |

(21) Production of citrulline from lactose-containing material

*Corynbacterium glutamicum* K61 (FERM BP-1111) (arginine-requiring) was transformed with pCPL7 by the same method as in (7) above, and it was confirmed that the transformant thus obtained carried pCPL7.

Citrulline production test on the transformant and the parent strain was carried out under the same conditions as in the ornithine production test described in (20) above. The results are shown in Table 21.

TABLE 21

| Strain | L-Citrulline (g/l) |
| --- | --- |
| Corynebacterium glutamicum K61 (FERM BP-1111) | 0.02 |
| Corynebacterium glutamicum K61/pCPL7 | 0.5 |

(22) Production of proline from lactose-containing material

Corynbacterium glutamicum H-3334 (FERM P-6823) (6-mercaptoguanosine-resistant) was transformed with pCPL7 by the same method as in (7) above, and it was confirmed that the transformant thus obtained carried pCPL7.

Proline production test on the transformant and the parent strain was carried out in the following manner:

Each strain was cultured with shaking in a seed medium (pH 7.2) comprising 10 g/l glucose, 5 g/l meat extract, 10 g/l peptone, 3 g/l yeast extract and 3 g/l NaCl at 30° C. for 24 hours. For the culture of the transformant, spectinomycin was added to a seed medium at a concentration of 100 µg/ml. Then, 2 ml of the seed culture was inoculated into 20 ml of a production medium (pH 7.4) comprising 100 g/l (as lactose) whey powder, 10 g/l $(NH_4)_2SO_4$, 3 g/l $KH_2PO_4$, 0.5 g/l $MgSO_4 \cdot 7H_2O$, 10 mg/l $FeSO_4 \cdot 7H_2O$, 10 mg/l nicotinic acid, 100 µg/l thiamine hydrochloride, 100 µg/l biotin, 20 g/l corn steep liquor, 20 g/l sodium L-glutamate and 30 g/l $CaCO_3$ in a 300 ml-Erlenmeyer flask, and shaking culture was carried out at 32° C. for 96 hours. After the culturing was finished, the amount of L-proline formed in the culture filtrate was determined by the method of Chinard [J. Biol. Chem., 199, 91 (1952)]. The results are shown in Table 22.

TABLE 22

| Strain | L-Proline (g/l) |
| --- | --- |
| Corynebacterium glutamicum H-3334 (FERM P-6823) | 0.2 |
| Corynebacterium glutamicum H-3334/pCPL7 | 5.1 |

What is claimed is:

1. A process for producing amino acids which comprises:
   providing a microorganism belonging to the genus Corynbacterium or Brevibacterium and carrying a recombinant DNA which confers the ability to assimilate lactose on microorganisms incapable of assimilating lactose, said recombinant DNA comprising:

(a) an EcoRI-SalI-cleaved DNA fragment of 3.2 kb containing the structural gene lacy which is obtained from Escherichia coli lactose operon, (b) an EcoRI-cleaved DNA fragment of 3.0 kb containing the structural gene lacZ which is obtained from pMC1871, and (c) a DNA fragment containing a promoter derived from a microorganism belonging to the genus Corynbacterium or Brevibacterium, which is positioned upstream of the said DNA fragments, culturing said microorganism in a medium containing lactose as a main carbon source to form an amino acid and, recovering said amino acid accumulated in the culture medium.

2. A process for producing amino acids according to claim 1, wherein said amino acid is glutamic acid, glutamine, lysine, threonine, isoleucine, valine, leucine, tryptophan, phenylalanine, tyrosine, histidine, arginine, ornithine, citrulline or proline.

3. A process for producing amino acids according to claim 1, wherein said recombinant DNA is plasmid pCPL7.

4. A process for producing amino acids according to claim 1, wherein said microorganism is Corynbacterium glutamicum K74 (FERM BP-1179), Corynbacterium glutamicum ATCC 13761/pCPL7, Corynbacterium glutamicum RH6/pCPL7, Corynbacterium glutamicum ATCC 21660/pCPL7, Corynbacterium glutamicum N-222/pCPL7, Corynbacterium glutamicum K-55/pCPL7, Corynbacterium glutamicum K-38/pCPL7, Corynbacterium glutamicum K-43/pCPL7, Corynbacterium glutamicum H-d/pCPL7, Corynbacterium glutamicum ATCC 31833/pE-arg5, pCPL7, Corynbacterium glutamicum ATCC 13232/pCPL7, Corynbacterium glutamicum K61/pCPL7, Corynbacterium glutamicum H-3334/pCPL7, Corynbacterium herculis ATCC 13868/pCPL7, Brevibacterium flavum ATCC 14067/pCPL7, Brevibacterium flavum ATCC 21528/pCPL7, Brevibacterium lactofermentum ATCC 13869/pCPL7, Brevibacterium lactofermentum ATCC 21086/pCPL7, Brevibacterium lactofermentum KY-10614/pCPL7 or Brevibacterium lactofermentum ATCC 21888/pCPL7.

5. A biologically pure culture of Corynebacterium glutamicum K74 (FERM BP-1179).

* * * * *